US007816331B2

(12) United States Patent
Patel et al.

(10) Patent No.: US 7,816,331 B2
(45) Date of Patent: Oct. 19, 2010

(54) SUBSTITUTED INDAZOLE-O-GLUCOSIDES

(75) Inventors: Mona Patel, Belle Mead, NJ (US);
Philip J. Rybczynski, Branchburg, NJ (US); Maud Urbanski, Flemington, NJ (US); Xiaoyan Zhang, Belle Mead, NJ (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 12/564,421

(22) Filed: Sep. 22, 2009

(65) Prior Publication Data
US 2010/0062971 A1 Mar. 11, 2010

Related U.S. Application Data

(60) Continuation of application No. 12/337,875, filed on Dec. 18, 2008, now abandoned, which is a continuation of application No. 11/446,014, filed on Jun. 2, 2006, now Pat. No. 7,511,021, which is a division of application No. 10/903,034, filed on Jul. 30, 2004, now Pat. No. 7,084,124.

(60) Provisional application No. 60/579,722, filed on Jun. 15, 2004, provisional application No. 60/519,381, filed on Nov. 12, 2003, provisional application No. 60/491,523, filed on Aug. 1, 2003, provisional application No. 60/491,534, filed on Aug. 1, 2003.

(51) Int. Cl.
*A01N 43/04* (2006.01)
*A61K 31/70* (2006.01)

(52) U.S. Cl. .............................. 514/27; 514/23; 514/25

(58) Field of Classification Search ........................ None
See application file for complete search history.

(56) References Cited

U.S. PATENT DOCUMENTS

| | | | |
|---|---|---|---|
| 4,584,369 A | 4/1986 | Klein et al. | |
| 5,149,838 A | 9/1992 | Humphrey et al. | |
| 5,424,406 A | 6/1995 | Tsujihara et al. | |
| 5,731,292 A | 3/1998 | Tsujihara et al. | |
| 5,767,094 A | 6/1998 | Tsujihara et al. | |
| 5,780,483 A | 7/1998 | Widdowson et al. | |
| 5,830,873 A | 11/1998 | Tsujihara et al. | |
| 6,048,842 A | 4/2000 | Tsujihara et al. | |
| 6,153,632 A | 11/2000 | Rieveley | |
| 6,297,363 B1 | 10/2001 | Kubo et al. | |
| 6,414,126 B1 | 7/2002 | Ellsworth et al. | |
| 6,515,117 B2 | 2/2003 | Ellsworth et al. | |
| 6,562,791 B1 | 5/2003 | Maurya et al. | |
| 6,617,313 B1 | 9/2003 | Maurya et al. | |
| 6,627,611 B2 | 9/2003 | Tomiyama et al. | |
| 6,683,056 B2 | 1/2004 | Washburn et al. | |
| 6,774,112 B2 | 8/2004 | Gougoutas | |
| 7,084,124 B2 * | 8/2006 | Patel et al. | 514/27 |
| 7,511,021 B2 * | 3/2009 | Patel et al. | 514/27 |
| 2002/0032164 A1 | 3/2002 | Dale et al. | |
| 2003/0114390 A1 | 6/2003 | Washburn et al. | |

FOREIGN PATENT DOCUMENTS

| | | |
|---|---|---|
| EP | 579204 A2 | 1/1994 |
| WO | WO 01/16122 A1 | 3/2001 |
| WO | WO 01/16123 A1 | 3/2001 |
| WO | WO 01/27128 A1 | 4/2001 |
| WO | WO 01/64669 A1 | 9/2001 |
| WO | WO 01/68660 A1 | 9/2001 |
| WO | WO 01/74835 A1 | 10/2001 |
| WO | WO 01/74834 A1 | 11/2001 |
| WO | WO 02/083066 A1 | 10/2002 |
| WO | WO 02/098893 A1 | 12/2002 |
| WO | WO 03/000712 A1 | 1/2003 |
| WO | WO 03/011880 A1 | 2/2003 |
| WO | WO 03/020737 A1 | 3/2003 |
| WO | WO 03/080634 A1 | 10/2003 |
| WO | WO 03/087093 A1 | 10/2003 |
| WO | WO 2004/080990 A1 | 9/2004 |
| WO | WO 2004/087727 A1 | 10/2004 |

OTHER PUBLICATIONS

Hongu, M. et al. "Na+ -Glucose Cotransporter Inhibitors as Antidiabetic Agents. II. Synthesis and Structure-Activity Relationships of 4'-Dehydroxyphlorizin Derivatives", Chem. Pharm. Bull. 46(1) (1998), pp. 22-33.
Ohsumi, K. et al. "Pyrazole-O-Glucosides as Novel Na+ -Glucose Cotransporter (SGLT) Inhibitors" Bioorganic & Medicinal chemistry Letters 13 (2003) pp. 2269-2272.
Tanaka, H. et al. "Solid-Phase Synthesis of β-Mono-Substituted Ketones and an Application to the Synthesis of a Library of Phlorizin Derivatives", Letter (2002) pp. 1427-1430.
Somei, M. et al., "The First and Simple Total synthesis of Cappariloside A¹" Heterocycles, vol. 53, No. 7, (2000) pp. 1573-1578.
Tsujihara, K. et al., "Na+ -Glucose Cotransporter (SGLT) Inhibitors as Antidiabetic Agents. 4. Synthesis and Pharmacological Properties of 4'-Dehydroxyphlorrizin Derivatives Substituted on the B Ring", J. Med. Chem. (1999) 42, pp. 5311-5324.
Tsujihara, K. et al., "Na+ -Glucose Cotransporter (SGLT) Inhibitors as Antidiabetic Agents. 4. Synthesis and Pharmacological Properties of 4'-Dehydroxyphlorrizin Derivatives Substituted on the B Ring", Chem. Pharm. Bull. vol. 44, No. 6, (1996) pp. 1174-1180.
Fresneda, P.M. "Synthesis of the indole alkaloids meridianins from the tunicate *Aplidium meridianum*" Tetrahedron 57 (2001) pp. 2355-2363.
Ketcha, D. M. et al., "Synthesis of Alyl-Substituted N-Protected Indoles via Acylation and Reductive Deoxygenation1" J. Org. Chem. (1989) 54, pp. 4350-4356.
Blair, J.B. et al., "Effect of Ring Fluorination on the Pharmacology of Hallucinogenic Tryptamines", J. Med. Chem. (200), 43, 4701-4710.
Appleton, J.E. et al, "A Mild and Selective C-3 Reductive Alkylation of Indoles", Tetrahedron Letters, vol. 34, No. 9, (1993) pp. 1529-1532.

(Continued)

*Primary Examiner*—Traviss C McIntosh, III

(57) ABSTRACT

Substituted indazole-O-glucosides, compositions containing them, and methods of using them, for example for the treatment of diabetes and Syndrome X are disclosed.

14 Claims, No Drawings

OTHER PUBLICATIONS

Comins, D.L. et al., "Synthesis of 3-Substituted Indoles Via N-Acylindolium Ions", Tetrahedron Letters, vol. 27, No. 17, (1986) pp. 1869-1872.

Dillard, R.D. et al., "Indole Inhibitors of Human Nonpancreatic Secretory Phospholipase A2. 1. Indole-3-acetamides", J. Med. Chem. (1996) 39, pp. 5119-5136.

Ellsworth, B.A. et al.,"C-Arylglucoside synthesis: triisopropylsilane as a selective reagent for the reduction of an anomeric C-phenyl ketal" Tetrahedron: Ssymmetry 14 (2003) pp. 3243-3247.

Link, J.T. et al., "A method for preparing C-glycosides related to phlorizin" Tetrahedron Letters 41 (2000) pp. 9213-9217.

Czernecki, S. et al., "C-Glycosides. 7. Stereospecific C-Glycosylation of Aromatic and Heterocyclic Rings", J. Org. Chem. 54, (1989) pp. 610-612.

Dondoni, A. et al., "Stereoselective synthesis of C-glycosylphosphonates from their ketols. Reconsideration of an abandoned route", Tetrahedron: Asymmetry 11 (2000) pp. 305-317.

Benhaddou, R. et al.,"Tetra-n-propylammonium tetra-oxoruthenate (VII): a reagent of choice for the oxidation of diversely protected glycopyranosses and glycofuranoses to lactones", Carbohydrate Research 260 (2994) pp. 243-250.

Dondoni, A. et al., "Thiazole-Based Synthesis of Formyl C-Glycosides", J. Org. Chem. 59 (1994) pp. 6404-6412.

Brooks, Paige R. et al., "Boron Trichloride/Tetra-n-Butylammonium Iodide: A Mild, Selective Combination Reagent for the Cleavage of Primary Alkyl Aryl Ethers", J. Org. Chem. (1999), 64, pp. 9719-9721.

Boehm, H-J et al., "Novel Inhibitors of DNA Gyrase: 3D Structure Based Biased Needle Screening, Hit Validation by Biophysical Methods, and 3D Guided Optimization. A Promising alternative to Random Screening", J. Med. chem. (200), 43, 2664-2674.

Orjales, A. et al. "New 2-Piperazinylbenzimidazole Derivatives as 5-HT3 Antagonists. Synthesis and Pharmacological Evaluation" J. Med. Chem. (1997), 40, pp. 586-593.

Mewshaw, R.E. et al., "New Generation Dopaminergic Agents. 7. Heterocyclic Bioisosteres That Exploit The 3-OH-Phenoxyethylamine D2 Template", Bioorganic & Medicinal Chemistry Letters 9 (1999) pp. 2593-2598.

Wolff, Manfred E., "Burger's Medicinal Chemistry, 5ed., Part 1", John Wiley & Sons, 1995, pp. 975-977.

Banker, G.S. et al., "Modern Pharmaceutics, 3ed.", Marcel Dekker, New York, 1996, p. 596.

Goodman & Gilman's: The Pharmacological Basis of Therapeutics, 10th Edition, McGraw-Hill Medical Publishing Division, 2001,pp. 54-56.

Unger et al., "Hyperglycaemia as an inducer as well as a consequence of impaired isle cell function and insulin resistance: implications for the management of diabetes.", Diabetologia, 1985, vol. 28, pp. 119-121.

Rosetti et al., "Glucose Toxicity.", Diabetes Cares, 1990, vol. 13, (6), pp. 610-630, *abstract only*.

Rosetti et al., "Correction of Hyperglycemia with Phlorizin Normalizes Tissue Sensitivity to Insulin in Diabetic Rats.", Journal of Clinical Investigation, 1987, vol. 79, (5), pp. 1510-1515.

Peng et al., "Post-transcriptional regulaton of Na+/Glucose Cotransporter (*SGTL1*) Gene Expression in LLC-PK1 Cells.", Journal of Biological Chemistry, 1995, vol. 270 (35), pp. 20536-20542.

PCT International Search Report dated Apr. 5, 2005 for PCT/US04/24626 which relates to U.S. Appl. No. 10/903,034.

* cited by examiner

SUBSTITUTED INDAZOLE-O-GLUCOSIDES

CROSS REFERENCE TO RELATED APPLICATIONS

This application is a continuation of U.S. Ser. No. 12/337,875, filed Dec. 18, 2008, now abandoned which is a continuation application of U.S. Ser. No. 11/446,014, filed Jun. 2, 2006, now U.S. Pat. No. 7,511,021, which is a divisional of U.S. Ser. No. 10/903,034, filed Jul. 30, 2004, now U.S. Pat. No. 7,084,124, which claims benefit of provisional applications Ser. No. 60/579,722, filed 15 Jun. 2004; Ser. No. 60/519,381, filed 12 Nov. 2003; Ser. No. 60/491,523, 1 filed August 2003; and Ser. No. 60/491,534, filed 1 Aug. 2003, each of which is incorporated by reference herein.

FIELD OF THE INVENTION

This invention relates to substituted indazole-O-glucosides, compositions containing them, and methods of using them, for example, for the treatment or prophylaxis of diabetes and Syndrome X.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity.

Therapy for IDDM patients has consistently focused on administration of exogenous insulin, which may be derived from various sources (e.g., human, bovine, porcine insulin). The use of heterologous species material gives rise to formation of anti-insulin antibodies which have activity-limiting effects and result in progressive requirements for larger doses in order to achieve desired hypoglycemic effects.

Typical treatment of Type II diabetes mellitus focuses on maintaining the blood glucose level as near to normal as possible with lifestyle modification relating to diet and exercise, and when necessary, the treatment with anti-diabetic agents, insulin or a combination thereof. NIDDM that cannot be controlled by dietary management is treated with oral antidiabetic agents.

Although insulin resistance is not always treated in all Syndrome X patients, those who exhibit a prediabetic state (e.g., IGT, IFG), where fasting glucose levels may be higher than normal but not at the diabetes diagnostic criterion, is treated in some countries (e.g., Germany) with metformin to prevent diabetes. The anti-diabetic agents may be combined with pharmacological agents for the treatment of the concomitant co-morbidities (e.g., antihypertensives for hypertension, hypolipidemic agents for lipidemia).

First-line therapies typically include metformin and sulfonylureas as well as thiazolidinediones. Metformin monotherapy is a first line choice, particularly for treating type II diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line treatment option. Another first line therapy choice may be thiazolidinediones. Alpha glucosidase inhibitors are also used as first and second line therapies. Patients who do not respond appropriately to oral anti-diabetic monotherapy, are given combinations of the above-mentioned agents. When glycemic control cannot be maintained with oral antidiabetics alone, insulin therapy is used either as a monotherapy, or in combination with oral antidiabetic agents.

One recent development in treating hyperglycemia is focused on excretion of excessive glucose directly into urine. Specific inhibitors of SGLTs have been shown to increase the excretion of glucose in urine and lower blood glucose levels in rodent models of IDDM and NIDDM.

SUMMARY OF THE INVENTION

One aspect of the present invention is directed to compounds, methods and compositions for the treatment or prophylaxis of diabetes, Syndrome X, or associated symptoms or complications. More specifically, this invention is directed to a method of treating diabetes or Syndrome X, or associated symptoms or complications thereof, in a subject afflicted with such a condition, said method comprising the step of administering one or more glucose reabsorption inhibitors disclosed herein. According to one aspect of the invention, said method of treatment can further comprise the step of administering one or more additional antidiabetic agents, such as a second antidiabetic agent or a second and a third antidiabetic agent.

Another aspect of the invention features a compound of formula (II):

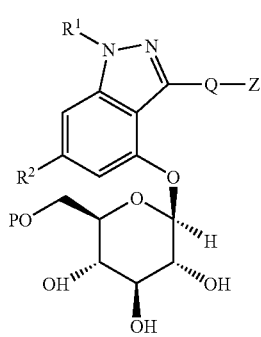

wherein

R¹ is H or $C_{1-4}$ alkyl;

R² is H, F, Cl, methoxy, or $C_{1-3}$ alkyl;

Q is —$(CH_2)_n$— where n is 0, 1, or 2; or, where R² is H, F, Cl, or methoxy, then Q can also be selected from —$CH_2$—S;

Z is substituted or unsubstituted, and is selected from $C_{3-7}$ cycloalkyl, phenyl, benzhydryl, a 5- or 6-membered heteroaryl having 1 or 2 heteroatoms independently selected from N, O, and S, a biaryl, a 9- or 10-membered fused bicyclyl (such as naphthyl), and a fused heterobicyclyl, wherein said fused heterobicyclyl has between 1 and 4 heteroatoms (and preferably between 1 and 3 or between 1 and 2 heteroatoms) independently selected from N, O, and S;

P=H or acetyl;

or a pharmaceutically acceptable salt, amide, or ester thereof.

One aspect of the invention features a pharmaceutical composition comprising a glucose reabsorption inhibitor, at least one additional anti-diabetic agent (such as one, two, three additional anti-diabetic agents), and a pharmaceutically acceptable carrier. The invention also provides a process for formulating a pharmaceutical composition, comprising formulating together a glucose reabsorption inhibitor, a second anti-diabetic agent, and a pharmaceutically acceptable carrier.

An embodiment of the invention is a method for treating diabetes or Syndrome X, or associated symptoms or complications thereof in a subject, said method comprising administering to said subject a jointly effective amount of a glucose reabsorption inhibitor and administering to said subject a jointly effective amount of a second anti-diabetic agent, said combined administration providing the desired therapeutic effect.

Another embodiment of the invention is a method for inhibiting the onset of diabetes or Syndrome X, or associated symptoms or complications thereof in a subject, said method comprising administering to said subject a jointly effective dose of a glucose reabsorption inhibitor and administering to said subject a jointly effective amount of an second anti-diabetic agent, said combined administration providing the desired prophylactic effect.

In the disclosed methods, the diabetes or Syndrome X, or associated symptoms or complications thereof, is selected from IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

Also included in the invention is the use of one or more glucose reabsorption inhibitors in combination with one or more anti-diabetic agents for the preparation of a medicament for treating a condition selected from IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

DETAILED DESCRIPTION OF THE INVENTION

All diabetics, regardless of their genetic and environmental backgrounds, have in common an apparent lack of insulin or inadequate insulin function. Because transfer of glucose from the blood into muscle and fatty tissue is insulin dependent, diabetics lack the ability to utilize glucose adequately, which leads to undesired accumulation of glucose in the blood (hyperglycemia). Chronic hyperglycemia leads to decrease in insulin secretion and contributes to increased insulin resistance, and as a result, the blood glucose concentration is increased so that diabetes is self-exacerbated (Diabetologia, 1985, "Hyperglycaemia as an inducer as well as a consequence of impaired isle cell function and insulin resistance: implications for the management of diabetes", Vol. 28, p. 119); Diabetes Cares, 1990, Vol. 13, No. 6, "Glucose Toxicity", pp. 610-630). Therefore, by treating hyperglycemia, the aforementioned self-exacerbating cycle is interrupted so that the prophylaxis or treatment of diabetes is made possible.

U.S. Pat. No. 6,153,632 to R. Rieveley discloses a method and composition stated to be for the treatment of diabetes mellitus (Type I, Impaired Glucose Tolerance ["IGT"] and Type II), which incorporates a therapeutic amount of one or more insulin sensitizers along with one or more of an orally ingested insulin, an injected insulin, a sulfonylurea, a biguanide or an alpha-glucosidase inhibitor for the treatment of diabetes mellitus.

According to one aspect, the invention features the combination of a PPAR modulator, preferably a PPAR δ agonist, and an SGLT inhibitor, preferably an SGLT 2 inhibitor or a selective SGLT 2 inhibitor.

A. TERMS

Some terms are defined below and by their usage throughout this disclosure.

Unless otherwise noted, "alkyl" and "alkoxy" as used herein, whether used alone or as part of a substituent group, include straight, cyclic, and branched-chain alkyl having 1 to 8 carbon atoms, or any number within this range. For example, alkyl radicals include methyl, ethyl, n-propyl, isopropyl, n-butyl, isobutyl, sec-butyl, t-butyl, 2-butenyl, 2-butynyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. The alkyl and alkoxy group may be independently substituted with one to five, preferably one to three groups selected from halogen (F, Cl, Br, I), oxo, OH, amino, carboxyl, and alkoxy. The alkyl and alkoxy group may also be independently linked to one or more PEG radicals (polyethylene glycol).

The term "acyl" as used herein, whether used alone or as part of a substituent group, means an organic radical having a carbonyl group linked to hydrocarbyl group having 1 to 7 carbon atoms (branched or straight chain or cyclic) derived from an organic acid by removal of the hydroxyl group. For example C₄ acyl can include (CO)CH₂CH₂CH₂CH₃ and (CO)(CH₂(CH)(CH₃)₂; similarly, C₆ acyl includes both (CO)(C₆H₁₃) and (CO)(C₆H₅). The term "Ac" as used herein, whether used alone or as part of a substituent group, means acetyl.

"Aryl" is a carbocyclic aromatic radical including, but not limited to, phenyl, 1- or 2-naphthyl and the like. The carbocyclic aromatic radical may be substituted by independent replacement of 1 to 3 of the hydrogen atoms thereon with halogen, OH, CN, mercapto, nitro, amino, cyano, optionally substituted C₁-C₈-alkyl, optionally substituted alkoxy, alkylthio, alkylsulfinyl, alkylsulfonyl, alkyl-amino, di(C₁-C₈-alkyl)amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —CONH₂, alkyl-O—CO—O—, or alkyl-CO—NH—. Illustrative aryl radicals include, for example, phenyl, naphthyl, biphenyl, indene

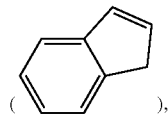

indane

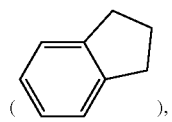

fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

The term "heteroaryl" as used herein represents a stable five or six-membered monocyclic or bicyclic aromatic ring system which consists of carbon atoms and from one to three heteroatoms selected from N, O and S. The heteroaryl group may be attached at any heteroatom or carbon atom, which results in the creation of a stable structure. Examples of heteroaryl groups include, but are not limited to benzofuranyl, benzothiophenyl, pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Preferred heteroaryl groups include pyridinyl, thiophenyl, furanyl, and quinolinyl. When the heteroaryl group is substituted, the heteroaryl group may have one to three substituents which are independently selected from halogen, OH, CN, mercapto, nitro, amino, cyano, optionally substituted C₁-C₈-alkyl, optionally substituted alkoxy, alkylthio, alkylsulfinyl, alkylsulfonyl, alkyl-amino, di(C₁-C₈-alkyl)amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —CONH₂, alkyl-O—CO—O—, or alkyl-CO—NH—.

The terms "heterocycle," "heterocyclic," and "heterocyclyl" refer to an optionally substituted, fully or partially saturated, aromatic or nonaromatic, cyclic group which is, for example, a 4- to 7-membered monocyclic, 7- to 11-membered bicyclic ("heterobicyclyl") (such as 9-10 bicyclic), or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary heterobicyclyl groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; benzimidazolyl; benzthiazolyl; and the like. When the heteroaryl group is substituted, the heterocyclyl may be independently substituted with one to five, preferably one to three groups selected from halogen, OH, CN, mercapto, nitro, amino, cyano, optionally substituted C₁-C₈-alkyl, optionally substituted alkoxy, alkylthio, alkylsulfinyl, alkylsulfonyl, alkyl-amino, di(C₁-C₈-alkyl)amino, formyl, carboxyl, alkoxycarbonyl, alkoxycarbonyloxy, alkanoyloxy, phenyl, carbamoyl, carboxamide, di-lower alkylcarbamoyloxy, phenoxycarbonyloxy group, lower alkylenedioxy, benzoyloxy, alkyl-CO—O—, alkyl-O—CO—, —CONH₂, alkyl-O—CO—O—, or alkyl-CO—NH—.

The term "biaryl" includes a heteroaryl linked to a phenyl, a phenyl linked to a heteroaryl (such as furan, pyridine, thiophene), and a phenyl linked to a phenyl. Examples of phenyl-phenyl, heteroaryl-phenyl, substituted heteroaryl-phenyl, and phenyl-heteroaryl, respectively, include:

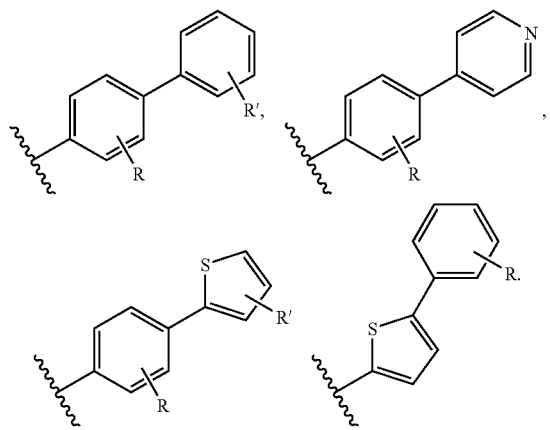

The term "composition" is intended to encompass a product comprising the specified ingredients in the specified amounts, as well as any product which results, directly or indirectly, from combinations of the specified ingredients in the specified amounts.

The term "combined administration" includes co-administration wherein: 1) the two or more agents are administered to a subject at substantially similar times; and 2) the two or more agents are administered to a subject at different times, at independent intervals which may or may not overlap or coincide.

The term "subject" as used herein, refers to an animal, preferably a mammal, most preferably a human, who is the object of treatment, observation or experiment.

The term "RXR modulator" as used herein, refers to Retinoid-X receptor agonists, partial agonists, or antagonists. Preferably the modulator increases insulin sensitivity. According to one aspect, the modulator is an RXR agonist.

Diabetes, Syndrome X, and associated symptoms or complications include such conditions as IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts. Examples of a prediabetic state includes IGT and IFG.

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated by the modulation of glucose reabsorption activity or other antidiabetic activity or both. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art. Examples of hydroxyl and diol protecting groups are provided below.

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacol methyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl) ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, and polyethyleneglycol ethers.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(/midazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio)pentanoate, pivaloate, adamantoate, crotonate, 4-methoxycrotonate, benzoate, p-phenylbenzoate, 2,4, 6-trimethylbenzoate (mesitoate), and polyethyleneglycol esters.

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate, and polyethyleneglycol carbonates.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Glucose Reabsorption Inhibitors

One method of treating hyperglycemia is to excrete excessive glucose directly into urine so that the blood glucose concentration is normalized. For example, sodium-glucose cotransporters (SGLTs), primarily found in chorionic membrane of the intestine and the kidney, are a family of proteins actively involved in the normal process of glucose absorption. Among them, SGLT1 is present in intestinal and renal epithelial cells (Lee et al., 1994), whereas SGLT2 is found in the epithelium of the kidney (You et al., 1995, MacKenzie et al., 1994). Glucose absorption in the intestine is primarily mediated by SGLT1, a high-affinity low-capacity transporter with a $Na^+$:glucose transport ratio of 2:1. SGLT2, also known as SAAT1, transports $Na^+$ and glucose at a ratio of 1:1 and functions as a low-affinity high-capacity transporter. These SGLTs are characterized in Table 1:

TABLE 1

| ISOFORM | TISSUE | Stoichiometry | Preferred Substrate | $K_m$* in vitro | TmG** in vitro | $K_m$* In vivo |
|---|---|---|---|---|---|---|
| SGLT1 | Sm. Intestine | 2:1 | D-glucose D-galactose | 0.1 | nd | Nd |
|  | Kidney (S1, S3) | 2:1 | D-glucose D-galactose | 0.39 | 7.9 | 0.3 |
| SGLT2 (SAAT1) | Kidney (S3) | 1:1 | D-glucose | 1.64 | 83 | 6 |

*(mM) for D-glucose
**Maximal transport rate pmol/min/mm

Renal reabsorption of glucose is mediated by SGLT1 and SGLT2 (Silverman et al., 1992; Deetjen et al., 1995). Plasma glucose is filtered in the glomerulus and is transepithelially reabsorbed in the proximal tubules. SGLT1 and SGLT2 are located in the apical plasma membranes of the epithelium and derive their energy from the inward sodium gradient created by the $Na^+/K^+$ ATPase pumps located on the basolateral membrane. Once reabsorbed, the elevated cytosolic glucose is then transported to the interstitial space by facilitated glucose transports (GLUT1 and GLUT2). Therefore, inhibition of SGLTs reduces plasma glucose through suppression of glucose reabsorption in the kidney. A therapeutically or prophylactically effective amount of an SGLT inhibitor, such as that sufficient to increase urine glucose excretion, or to decrease plasma glucose, in a subject by a desired amount per day, can be readily determined using methods established in the art. Recently, it has been found that phlorizin, a natural glycoside present in barks and stems of Rosaceae (e.g., apple, pear, etc.), inhibits $Na^+$-glucose co-transporters located in chorionic membrane of the intestine and the kidney. By inhibiting $Na^+$-glucose co-transporter activity, phlorizin inhibits the renal tubular glucose reabsorption and promotes the excretion of glucose so that the glucose level in a plasma is controlled at a normal level for a long time via subcutaneous daily administration (Journal of Clinical Investigation, 1987, Vol. 79, p. 1510).

Other SGLT inhibitors include alkyl- and phenyl-glucosides, 1-5-isoquinolinesulfonyl)-2-methylpiperazine-HCl (indirectly via protein kinase C), p-chloromercuribenzoate (PCMB), N,N'-dicyclohexylcarbodiimide (DCCD), copper and cadmium ions, and trivalent lanthanides.

B. COMPOUNDS

The invention features compounds of Formula (II):

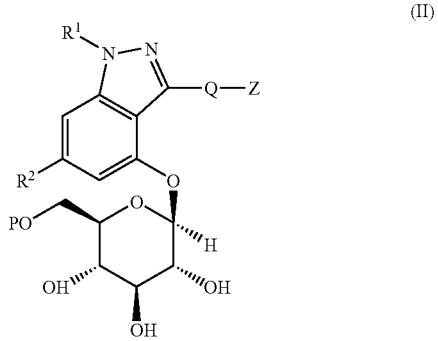

(II)

wherein $R^1$ is H or $C_{1-4}$ alkyl;

$R^2$ is H, F, Cl, methoxy, or $C_{1-3}$ alkyl;

Q is —$(CH_2)_n$— where n=0, 1, or 2; or, where $R^2$ is H, F, Cl, or methoxy, then Q can also be selected from —$CH_2$—S—;

P=H or acetyl;

Z is substituted or unsubstituted, and is selected from $C_{3-7}$ cycloalkyl, phenyl, benzhydryl, 5- or 6-membered heteroaryl having 1 or 2 heteroatoms independently selected from N, O, and S, a biaryl, a 9- or 10-membered fused bicyclyl or fused heterobicyclyl, wherein each fused heterobicyclyl has between 1 and 4 heteroatoms (and preferably between 1 and 2 heteroatoms) independently selected from N, O, and S.

Examples of preferred compounds of Formula (II) include:

(a) $R^1$ is H; (b) $R^2$ is H, methyl, or ethyl; (c) Q is $(CH_2)_n$— and n is 1 or 2; (d) Z is independently substituted with between 1 and 3 substituents independently selected from $C_{1-4}$ alkoxy, $C_{1-4}$ alkyl, $C_{3-6}$ cycloalkyl, halo, hydroxy, cyano, amino, $C_{1-4}$ alkylthio, $C_{1-4}$ aminoalkyl, mono- or dialkylamino, phenyl, 5-6 membered heterocyclyl containing between 1 and 3 heteroatoms independently selected from N, S, and O; and wherein the substituent(s) on Z can be further independently substituted with between 1 and 3 substituents independently selected from $C_{1-4}$ alkoxy, $C_{1-4}$ alkyl, halo, hydroxy, cyano, amino, $C_{1-4}$ alkylthio phenoxy, —$CONR^aR^b$, —$NHSO2R^a$, and —$SO_2NR^aR^b$;

(e) Z is phenyl, cyclopentyl, cyclohexyl, 4-substituted cyclohexyl, 2- or 3-substituted cyclopentyl, 4-substituted phenyl, 3,4-disubstituted phenyl, substituted thiophene, thiophenyl, benzofuranyl, dihydrobenzofuranyl, 4-substituted pyridyl, benzo[b]thienyl, chromanyl, benzothiophenyl, indanyl, naphthyl, 5,6,7,8-tetrahydronapthyl, 1,2,3,4-tetrahydronaphthyl, or benzo[1,4]dioxan; (f) limitations of (e) wherein Z is unsubstituted or substituted with between 1 and 2 substituents independently selected from methoxy, ethoxy, fluoro, chloro, methyl, ethyl, propyl, isopropyl, cyclopropyl, and phenyl; (g) Z is biphenyl, 4-ethylphenyl, (4-propyl)phenyl, 4-methoxyphenyl, 4-ethoxyphenyl, 4-methylthiophenyl, benzofuran-5-yl, dihydrobenzofuran-5-yl, naphthyl, or dihydrobenzofuran-6-yl, or (5-ethylthio)phenyl; (h) $R^1$ is H; and $R^2$ is H, methyl, ethyl, propyl, or isopropyl;

(i) Q is —$(CH_2)_n$—; n is 1 or 2; and $R^2$ is H, methyl, or ethyl; (i) limitation of (i) wherein $R^1$ is methyl; (j) limitation of (a) wherein $R^2$ is H, methyl, or ethyl; and Q is —$(CH_2)_n$— and n is 1 or 2; Z is phenyl, cyclopentyl, cyclohexyl, 4-substituted cyclohexyl, 2- or 3-substituted cyclopentyl, 4-substituted phenyl, 3,4-disubstituted phenyl, substituted thiophene, thiophenyl, biaryl, benzofuranyl, dihydrobenzofuranyl, 4-substituted pyridyl, benzo[b]thienyl, benzothiophenyl, indanyl, naphthyl, 5,6,7,8-tetrahydronapthyl, 1,2,3,4-tetrahydronaphthyl, or benzo[1,4]dioxan; and wherein Z is unsubstituted or substituted with between 1 and 2 substituents independently selected from methoxy, ethoxy, fluoro, chloro, methyl, ethyl, propyl, isopropyl, cyclopropyl, phenyl; (k) $R^2$ is H, methyl, or ethyl; wherein Q is —$(CH_2)_n$— and n is 1 or 2; and Z is biphenyl, 4-ethylphenyl, (4-propyl)phenyl, 4-methoxyphenyl, 4-ethoxyphenyl, 4-methylthiophenyl, benzofuran-5-yl, dihydrobenzofuran-5-yl, naphthyl, or dihydrobenzofuran-6-yl, or (5-ethylthio)phenyl; (l) and combinations of the above.

Examples of preferred compounds include: 2-{3-[2-(2,3-Dihydro-benzofuran-5-yl)-ethyl]-6-methyl-1H-indazol-4-yloxy}-β-D-glucopyranoside; 2-[3-(2-Benzofuran-5-yl-ethyl)-6-methyl-1H-indazol-4-yloxy]-β-D-glucopyranoside; 2-{3-[2-(2,3-Dihydro-benzofuran-5-yl)-ethyl]-1,6-dimethyl-1H-indazol-4-yloxy}-β-D-glucopyranoside; 2-{3-[2-(2,3-Dihydro-benzofuran-5-yl)-ethyl]-6-ethyl-1H-indazol-4-yloxy}-β-D-glucopyranoside and 2-[3-(4-Methoxy-benzyl)-6-methyl-1H-indazol-4-yloxy]-β-D-glucopyranoside.

Additional preferred compounds include: 2-[3-(2-Benzofuran-5-yl-ethyl)-1H-indazol-4-yloxy]-β-D-glucopyranoside; 2-{3-[2-(6-Methoxy-naphthalen-2-yl)-ethyl]-6-methyl-1H-indazol-4-yloxy}-β-D-glucopyranoside; 2-{3-[2-(2,3-Dihydro-benzo[1,4]dioxin-6-yl)-ethyl]-6-methyl-1H-indazol-4-yloxy}-β-D-glucopyranoside; 2-{3-[2-(4-Ethoxy-phenyl)-ethyl]-6-methyl-1H-indazol-4-yloxy}-β-D-glucopyranoside; 2-{6-Methyl-3-[2-(5,6,7,8-tetrahydro-naphthalen-2-yl)-ethyl]-1H-indazol-4-yloxy}-β-D-glucopyranoside; 2-[6-Methyl-3-(2-naphthalen-2-yl-ethyl)-1H-indazol-4-yloxy]-β-D-glucopyranoside; 2-{3-[2-(4-Methoxy-phenyl)-ethyl]-6-methyl-1H-indazol-4-yloxy}-β-D-glucopyranoside; 2-{3-[2-(6-Methoxy-5,6,7,8-tetrahydro-naphthalen-2-yl)-ethyl]-6-methyl-1H-indazol-4-yloxy}β-D-glucopyranoside and 2-[3-(2-Benzofuran-5-yl-ethyl)-6-methyl-1H-indazol-4-yloxy]-6-O-acetyl-β-D-glucopyranoside.

Additional preferred compounds include: 2-{3-[2-(6-Methoxy-1,2,3,4-tetrahydro-naphthalen-2-yl)-ethyl]-6-methyl-1H-indazol-4-yloxy}-β-D-glucopyranoside; 2-{3-[2-(4-Chloro-phenyl)-ethyl]-6-methyl-1H-indazol-4-yloxy}β-D-glucopyranoside; 2-[3-(4-Methoxy-phenylsulfanylmethyl)-1H-indazol-4-yloxy]-β-D-glucopyranoside; 2-[3-(2-Cyclohexyl-ethyl)-6-methyl-1H-indazol-4-yloxy]-β-D-glucopyranoside; 2-[3-(2,3-Dihydro-benzofuran-5-ylmethyl)-6-methyl-1H-indazol-4-yloxy]-β-D-glucopyranoside; 2-{3-[2-(4-Trifluoromethyl-phenyl)-ethyl]-6-methyl-1H-indazol-4-yloxy}-β-D-glucopyranoside; 2-{3-[2-(4-Methanesulfonylamino-phenyl)-ethyl]-6-methyl-1H-indazol-4-yloxy}-β-D-glucopyranoside and 2-{3-[2-(2,3-Dihydro-benzofuran-5-yl)-ethyl]-6-methyl-1H-indazol-4-yloxy}-6-O-acetyl-β-D-glucopyranoside.

Additional preferred compounds include 2-[3-(4-Ethyl-benzyl)-6-methyl-1H-indazol-4-yloxy]-β-D-glucopyranoside; 2-[6-Methyl-3-(4-propyl-benzyl)-1H-indazol-4-yloxy]-β-D-glucopyranoside; 2-[3-(4-Methylsulfanyl-benzyl)-6-methyl-1H-indazol-4-yloxy]-β-D-glucopyranoside; 2-[3-(4-Biphenyl)-6-methyl-1H-indazol-4-yloxy]-β-D-glucopyranoside; 2-[3-(4-Cyclopropyl-benzyl)-6-methyl-1H-indazol-4-yloxy]-β-D-glucopyranoside and 2-[3-(5-Ethylthiophen-2-ylmethyl)-6-methyl-1H-indazol-4-yloxy]-β-D-glucopyranoside.

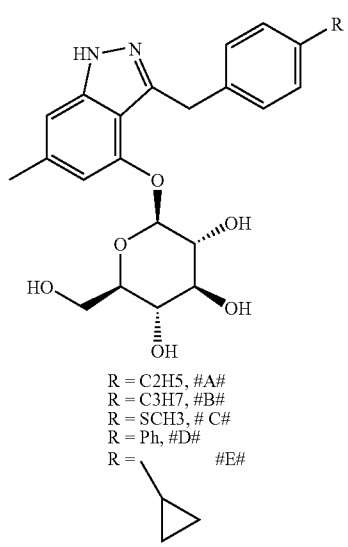

R = C2H5, #A#
R = C3H7, #B#
R = SCH3, #C#
R = Ph, #D#
R = #E#

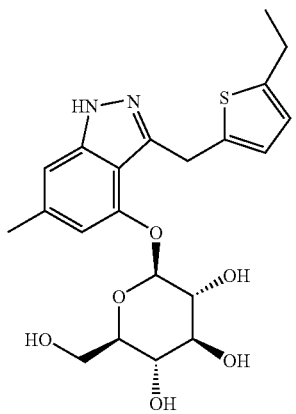

F#

The most preferred compounds are 2-{3-[2-(2,3-Dihydro-benzofuran-5-yl)-ethyl]-6-methyl-1H-indazol-4-yloxy}-β-D-glucopyranoside; 2-[3-(2-Benzofuran-5-yl-ethyl)-6-methyl-1H-indazol-4-yloxy]-β-D-glucopyranoside; 2-[3-(4-Ethyl-benzyl)-6-methyl-1H-indazol-4-yloxy]-β-D-glucopyranoside and 2-[3-(5-Ethylthiophen-2-ylmethyl)-6-methyl-1H-indazol-4-yloxy]-β-D-glucopyranoside.

C. SYNTHETIC METHODS

One aspect of the invention features substituted indazoles of Formula (II).

These compounds can be prepared according to traditional synthetic organic chemistry methods or according to combinatorial or matrix synthesis methods. The following three Schemes, narrative, and chemistry Examples 1-22 provide general guidance.

Scheme 1

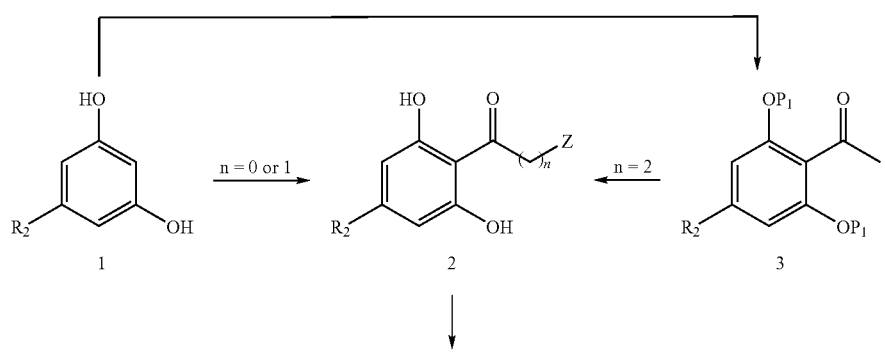

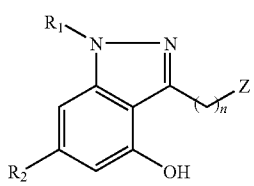

Compounds of this invention, wherein $R_2$ is as defined in Formula (II) and Z is an aromatic or a cycloalkyl ring, can be prepared as outlined in Schemes 1 and 3. As set forth in Scheme 1, compounds of Formula 1 are either commercially available (wherein $R_2$ is H, methyl or methoxy) or can be prepared by literature methods [when $R_2$ is chloro, ethyl, propyl, isopropyl: Tsujihara et al. J. Med. Chem. 1999 42, 5311-5324; when $R_2$ is fluoro: Brooks et al. J. Org. Chem. 1999, 64, 9719-9721] from commercially available materials. Compounds of Formula 2 wherein n is 0 or 1 can be prepared from compounds 1 by Friedel-Crafts acylation with an aryl acid chloride or an arylacetic acid using a Lewis acid, such as boron trifluoride diethyl etherate under neat conditions.

Compounds of Formula 3, where $P_1$ is benzyl (Bn) or methoxymethyl (MOM), can be prepared from compounds of Formula 1 by literature methods [Tsujihara et al. J. Med. Chem. 1999 42, 5311-5324]. Compounds of Formula 2 where n is 2 can be prepared from compounds of Formula 3 in either two or three steps. Aldol condensation with an aryl aldehyde under basic conditions, such as a potassium hydroxide, in an alcoholic solvent such as ethanol at temperatures from 20° C. to reflux, followed by catalytic hydrogenation of the resulting alkene under conditions such as Pd on charcoal in an alcoholic solvent such as ethanol under hydrogen pressure from 1-3 atmospheres. When $P_1$ is benzyl, the groups are cleaved during hydrogenation to yield compounds of Formula 2 directly. When $P_1$ is MOM, the intermediate from catalytic hydrogenation is treated with a mineral acid such as hydrochloric acid in a combination of solvents such as dioxane and isopropyl alcohol.

Alternatively compounds of Formula 3, where $P_1$ is benzyl, can be treated with a strong base such as lithium diisopropylamide at -78° C., followed by the addition of cycloalkyl carboxaldehyde at -30° C. The product is then hydrogenated to simultaneously reduce the double bonds and remove the phenol-protecting group, thereby providing compounds of Formula 2 wherein n is 2, and Z is cycloalkyl.

Compounds of Formula 4 where $R_1$ is H or methyl can be prepared by cyclization of compounds of Formula 2 with hydrazine or methylhydrazine in an alcoholic solvent such as ethylene glycol at temperatures ranging from 140° C. to 160° C. Alternatively, a compound of Formula 4 where $R_1$ is alkyl can be obtained in three steps from a compound of Formula 4 where $R_1$ is H.

The phenol group in a compound of Formula 4, where $R_1$ is H, can be selectively alkylated with benzyl bromide in a polar solvent such as acetone in the presence of a base such as potassium carbonate. The resulting indazole can be alkylated with an alkyl iodide, such as ethyl iodide, and a base such as cesium carbonate in DMF or some other polar organic solvent.

Deprotection of the phenol group under hydrogenation conditions, such as palladium on charcoal and hydrogen gas at pressures ranging from 1 to 3 atmospheres in a solvent such as methanol, ethanol, ethyl acetate and the like, will provide compounds of Formula 4 where $R_1$ is an alkyl group, such as ethyl.

Scheme 2

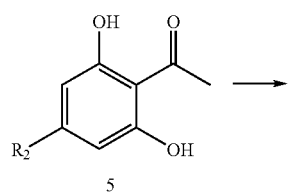

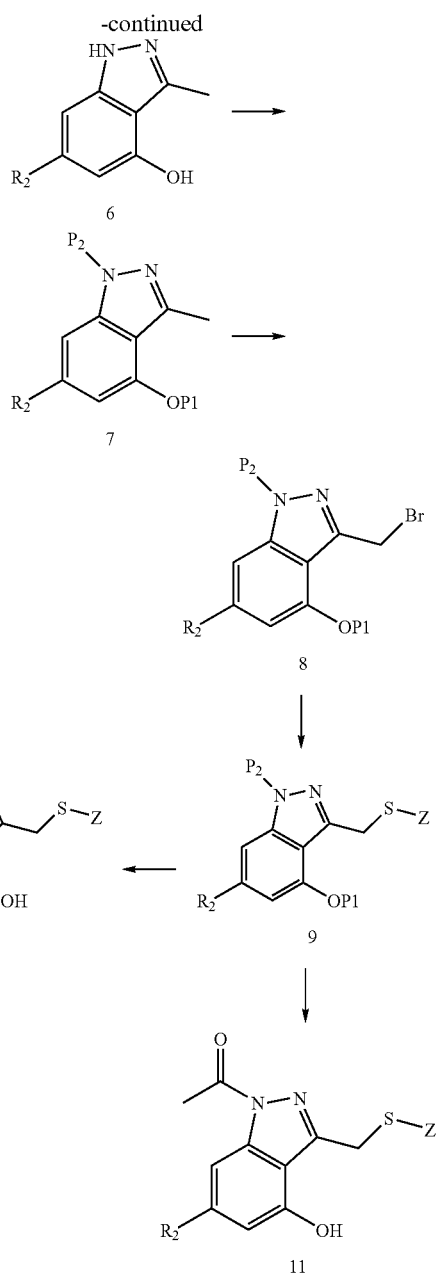

Compounds of this invention where $R_2$ is as defined in Formula (II), and Z is an aromatic ring, can be prepared as outlined in Schemes 2 and 3. Compounds of Formula 5 can be obtained from commercial sources or prepared by literature methods [Tsujihara et al. J. Med. Chem. 1999 42, 5311-5324]. A compound of Formula 6 can be prepared from a compound of Formula 5 by cyclization with hydrazine in an alcoholic solvent such as ethylene glycol at temperatures ranging from 140° C. to 160° C. Stepwise protection of a compound of Formula 6 provides a compound of Formula 7. Protection of the phenol can be accomplished with an ether-forming reagent such as tert-butyldimethylsilyl chloride and an amine such as imidazole in a polar solvent such as DMF, at temperature ranging from 0° C. to 80° C. Protection of the indazole nitrogen with a reagent such as di-tert-butyl dicarbonate in a solvent such as THF provides a compound of Formula 7 where $P_1$ is tert-butyldimethylsilyl and $P_2$ is t-butoxycarbonyl (BOC). The indazole nitrogen can also be protected with an acylating agent such as acetic anhydride, with or without a catalyst such as DMAP in a nonpolar solvent such as methylene chloride to yield a compound of Formula 7 where $P_2$ is acetyl (Ac). Subsequent bromination with a reagent such as N-bromosuccinimide (NBS) in the presence of a catalytic amount of benzoyl peroxide or 2,2'-azobisisobutyronitrile (AIBN) in a solvent such as carbon tetrachloride can provide compounds of Formula 8. A compound of formula 9 can then be obtained by reaction with an appropriately substituted thiophenol using a base such as triethylamine in a nonpolar solvent such as dichloromethane at temperatures ranging from 0° C.-50° C. The protecting groups $P_1$ (TBDMS) and $P_2$ (BOC) in a compound of Formula 9 can be removed simultaneously under acidic conditions such as aqueous HBr in a polar solvent such as DMF with potassium fluoride at room temperature to provide a compound of Formula 10. The acetyl (Ac) group $P_2$ of a compound of Formula 11 can be removed after glycosylation as described in Scheme 3.

method of treatment (treatment regimen) include, but are not limited to, the classes of compounds exemplified in Table 2.

TABLE 2

Combination Therapies with SGLT Inhibitors

| Mechanism or Class | Drug/Compound |
| --- | --- |
| Biguanide (class) | metformin |
|  | Fortamet (metformin XT) |
|  | metformin GR |
|  | metformin XL |
|  | NN-414 |
|  | fenofibrate/metformin combo |
| Insulin Secretagogue (mech), Sulfonylureas (class) | glimeparide |
|  | glyburide/glibenclamide combo |
|  | glyburide/metformin combo |

Scheme 3

Compounds of Formula 12, where $R_1$ is as defined in Formula II, can be obtained from compounds of Formula 4, 10 and 11, prepared in Schemes 1 and 2, by glycosidation of the phenol group with 2,3,4,6-tetra-O-acetyl-α-D-glucopyranosyl bromide in an appropriate solvent, such as acetone, acetonitrile or DMF under basic conditions, such as potassium carbonate or lithium carbonate, followed by deprotection of acetyl groups in an alcoholic solvent such as methanol using mild basic conditions such as potassium carbonate or sodium methoxide at room temperature. A compound of Formula 13 can be isolated as a by-product in the deprotection step.

D. ADDITIONAL ANTIDIABETIC AGENTS

Antidiabetic agents that can be used, according to aspects of the invention, as a second or a third antidiabetic agent in a pharmaceutical composition, a formulation, or a combination TABLE 2-continued Combination Therapies with SGLT Inhibitors

| Mechanism or Class | Drug/Compound |
| --- | --- |
|  | glipizide |
|  | glipizide/metformin combo |
|  | gliclazide |
|  | chlorpropamide |
|  | tolbutamide |
|  | tolazamide |
| Insulin Secretagogue (mech), Meglitinides (class) | repaglinide |
|  | nateglinide |
|  | mitiglinide |
| Alpha-glucosidase inhibitors (mech) | acarbose |

TABLE 2-continued

Combination Therapies with SGLT Inhibitors

| Mechanism or Class | Drug/Compound |
|---|---|
| | miglitol |
| | voglibose |
| | emiglitate |
| Insulin and Insulin analogues (class) | insulin lispro |
| | insulin glargine |
| | insulin detemir |
| | insulin glulisine |
| | insulin aspart |
| | human insulin (Humulin R) |
| | human insulin (Novolin R) |
| | human insulin (Novolin BR) |
| | insulin, zinc suspension (Humulin L) |
| | insulin NHP (Humulin N) |
| | insulin, zinc suspension (Novolin L) |
| | insulin NHP (Novolin N) |
| | insulin, zinc suspension (Humulin U) |
| | human insulin, regular and NHP mix (Humulin 50/50) |
| | human insulin, regular and NHP mix (Humulin 70/30) |
| | human insulin, regular and NHP mix (Novolin 70/30) |
| Inhaled insulin (class) | Exubera |
| | AERx Insulin Diabetes Management System |
| | AIR inhaled insulin |
| Oral insulin (class) | Oralin |
| PPARgamma (mech) | rosiglitazone |
| | rosiglitazone/metformin combo |
| | pioglitazone |
| | isaglitazone (netoglitazone, MCC-555) |
| | rosiglitazone/sulfonylurea |
| | ragaglitazar |
| | balaglitazone (NN-2344) |
| | R-483 |
| | rivoglitazone (CS-011) |
| | FK-614 |
| | SCD-DKY |
| | tesaglitazar |
| | T131 |
| | CLX0921 |
| | LY-293111 (VML-295) |
| | MBX 102 |
| | AA10090 |
| | CDDO (TP-155C) |
| | DRF-2189 |
| | PHT-46 |
| | farglitazar |
| | GW-7845 |
| | L-764406 |
| | NC-2100 |
| | PN 2022 (PN 2034) |
| PPARalpha/gamma dual agonists (mech) | MK767/MK0767 (KRP 297) |
| | muraglitazar (BMS-298585) |
| | tesaglitazar |
| | LY-818 |
| | oxeglitazar (EML-4156) |
| | LY-929 |
| | BVT-142 |
| | DRF-2655 |
| | DRF-4832 |
| | DRF-4158 |
| | LY-465608 |
| | KT6-207 |
| | LSN-862 |
| PPARalpha Agonist (mech) | Fenofibrate |
| | Gemfibrozil |
| | Clofibrate |
| | Ciprofibrate |

TABLE 2-continued

Combination Therapies with SGLT Inhibitors

| Mechanism or Class | Drug/Compound |
|---|---|
| | Benzafibrate |
| | K-111 |
| | LY518674 (LY674) |
| | KRP-101 |
| | NS-220 |
| | GW-9578 |
| | GW-7647 |
| | GW-9820 |
| | LF-200337 |
| | ST-1929 |
| | Wy-14643 |
| PPARdelta Agonist (mech) | GW501516 |
| | GW-1514 |
| | L-165041 |
| | GW 8547 |
| PPARalpha/delta Dual Agonist (mech) | GW-2433 |
| PPARgamma/delta Dual Agonist (mech) | |
| PPARalpha/gamma/delta Modulator (mech) | CLX-0940 |
| RXR Agonist (mech) | |
| Insulin Secretagogue (mech), GLP-1 analogue (class) | Exanatide injectable |
| | Exanatide LAR injectable |
| | Exanantide oral |
| | Liraglutide |
| GLP-1 agonist (mech) | exenatide (AC2993) |
| | liraglutide (NN2211) |
| | LY-307161 |
| | CJC-113 |
| | ZP10 |
| | GLP-1 |
| | BIM-51077 |
| DPPIV Inhibitor (mech) | LAF-237 |
| | P32/98 |
| | P93/01 |
| | NVP-728 |
| Lipase Inhibitor (mech) | Orlistat |
| | ATL962 |
| Glucokinase Activator (mech) | Ro 28-1675 |
| | Ro 27-4375 |
| beta-3 Agonist (mech) | LY-337604 |
| | L-796568 |
| | CP-331684 |
| | CP-331679 |
| | CP-114271 |
| | Rafabegron (TAK-677) |
| | YM-178 |
| | N5984 |
| | GW427353 |
| IBAT Inhibitor (mech) | AZD-7806 |
| | SC-990 |
| | SC-017 |
| | GW-264 |
| HM74a/HM74 Agonist (mech) | Acipimox |
| Glucocorticoid Antagonist (mech) | A348441 |
| | A362947 |
| | CP394531 |
| | CP409069 |
| | CP472555 |
| Glycogen Phosphorylase a Inhibitor (mech) | NN4201 |
| | Ingliforib (CP368296) |
| FXR Antagonist (mech) | GW-4064 |
| LXR Agonist (mech) | GW-3965 |
| | T-0901317 |
| | T-0314407 |
| FXR Antagonist (mech) | |
| GLP-1 Analogue (class) | Albugon |

TABLE 2-continued

Combination Therapies with SGLT Inhibitors

| Mechanism or Class | Drug/Compound |
|---|---|
| GSK-3beta Inhibitor (mech) | |
| PTP-1b Inhibitor (mech) | ISIS-113715 |
|  | KP102 |
| Amylin Receptor Agonist | Pramlintide (symlin/amylin) |
| NO Scavenger (mech) | NOX-700 |
| 11beta-Hydroxysteroid Dehydrogenase Inhibitor | BVT-3498 |
| Peptide YY hormone | AC162325 |
| Glucagon Antagonist (mech) | NN-2501 |
| PEPCK Inhibitor (mech) | R1438 |
| Somatotropin Release-inhibiting Factor (mech) | SOM230 |
| CPT-1 Inhibitor (mech) | ST1326 |
| Carboxypeptidase Inhibitor (mech) | MLN-4760 |
| Leptin analogue (class) | Metrileptin |

E. COMBINATIONS

The invention features a combination therapy comprising administering a glucose reabsorption inhibitor, such as an SGLT inhibitor, and one or more antidiabetic agents) for the treatment of diabetes or Syndrome X, or associated symptoms or complications thereof. The demonstrated efficacy of SGLT inhibitors in numerous models of NIDDM validates the utility of this drug alone for the treatment of NIDDM in humans. Since glucose reabsorption inhibitors have a mechanism of action distinct from that of RXR modulators, the disclosed combination with RXR modulators has the advantage of reducing the amount of either drug necessary to achieve combined therapeutic or pharmaceutical efficacy, relative to the use of either drug alone, thereby reducing one or more adverse side-effects, which often include weight gain, edema, cardiac hypertrophy, hepatohypertrophy, hypoglycemia, or hepatotoxicity, or any combination thereof.

The invention provides a method for treating diabetes or Syndrome X, or complications thereof in a subject, said method comprising administering to said subject a jointly effective amount of a glucose reabsorption inhibitor in combination with a jointly effective amount of one or more antidiabetic agents. In one aspect of the invention, the antidiabetic agent is an RXR agonist or antagonist that increases insulin sensitivity in the subject. Methods to determine the insulin sensitizing activity of an agent are well known in the art. For example, an insulin sensitizer can increase glucose tolerance in a subject in an oral glucose tolerance test.

Particularly, the diabetes or Syndrome X, or associated symptoms or complication thereof is selected from IDDM, NIDDM, IGT, and IFG.

This invention also provides a pharmaceutical composition comprising one or more glucose reabsorption inhibitors, one or more RXR modulators, and a pharmaceutically acceptable carrier. In one aspect of the invention, the RXR modulator is an RXR agonist that increases insulin sensitivity in the subject. In another aspect of the invention, the RXR modulator is an RXR antagonist that increases insulin sensitivity in the subject.

In particular, the glucose reabsorption inhibitor is a SGLT1 and/or SGLT2 inhibitor.

For use in medicine, the salt or salts of the compounds of Formula II or V refer to non-toxic "pharmaceutically acceptable salt or salts." Other salts may, however, be useful in the preparation of compounds according to this invention or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc. The compounds of Formula II or a pharmaceutically acceptable salt thereof, may include an intramolecular salt thereof, or a solvate or hydrate thereof.

F. ADMINISTRATION, FORMULATION, AND DOSAGES

The utility of the disclosed compounds, compositions, and combinations to treat disorders in glucose and lipid metabolism can be determined according to the procedures well known in the art (see the references listed below), as well as all the procedures described in U.S. Pat. Nos. 5,424,406, 5,731,292, 5,767,094, 5,830,873, 6,048,842, WO01/16123, and WO01/16122 which are incorporated herein by reference. The compound may be administered to a patient by any conventional route of administration, including, but not limited to, intravenous, oral, subcutaneous, intramuscular, intradermal and parenteral administration. Preferably, formulations are for oral administration.

The present invention also provides pharmaceutical compositions comprising one or more glucose reabsorption inhibitors of the invention and one or more antidiabetic agents in association with a pharmaceutically acceptable carrier.

The daily dosage of the products may be varied over a wide range from 1 to 1000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the patient to be treated. The compounds may be administered on a regimen of 1 to 2 times per day. The dosages, however, may be varied depending upon the requirement of the patients, the severity of the condition being treated and the compound being employed. The use of either daily administration or post-periodic dosing may be employed. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient or ingredients are mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of one or more disclosed glucose reabsorption inhibitors and one or more antidiabetic agents, or a pharmaceutically acceptable salt thereof. When referring to these preformulation compositions as homogeneous, it is meant that the active ingredient or ingredients are dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient or ingredients of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

Advantageously, the combinations of one or more glucose reabsorption inhibitors and one or more antidiabetic agents of the present invention may be administered in a single daily dose, or the total daily dosage may be administered in divided doses of two, three or four times daily. Furthermore, one or more glucose reabsorption inhibitors and/or one or more additional antidiabetic agents according to the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Wherein the present invention is directed to the administration of a combination, the compounds may be co-administered simultaneously, sequentially, or in a single pharmaceutical composition. Where the compounds are administered separately, the number of dosages of each compound given per day, may not necessarily be the same, e.g. where one compound may have a greater duration of activity, and will therefore, be administered less frequently.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

The novel compositions of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

From Formula (II) and other disclosed formulae it is evident that some compounds in the compositions of the invention may have one or more asymmetric carbon atoms in their structure. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereospecific reactions.

Some compounds in the compositions of the present invention may have various individual isomers, such as trans and cis, and various alpha and beta attachments (below and above the plane of the drawing). In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. Unless otherwise noted, the scope of the present invention is intended to cover all such isomers or stereoisomers per se, as well as mixtures of cis and trans isomers, mixtures of diastereomers and racemic mixtures of enantiomers (optical isomers) as well.

The therapeutic effect of the glucose reabsorption inhibitor administered alone or in combination with one or more additional antidiabetic agent(s) in treating diabetes, Syndrome X, or associated symptoms or complications can be shown by methods known in the art. The following examples of synthesis and combination treatment with SGLT inhibitors and antidiabetic agents are intended to illustrate the invention but not to limit it.

G. SYNTHETIC CHEMICAL EXAMPLES

The invention features substituted indazoles of formula (II) as described above in the Summary section, the description, and the appended claims. These disclosed compounds may be made according to traditional synthetic organic chemistry methods or according to matrix or combinatorial chemistry methods. The Schemes and the Examples below provide general guidance.

$^1$HNMR spectra were measured on a Brucker AC-300 (300 MHz) spectrometer using tetramethylsilane (TMS) as an internal standard.

Example 1

2-{3-[2-(2,3-Dihydro-benzofuran-5-yl)-ethyl]-6-methyl-1H-indazol-4-yloxy}β3-D-glucopyranoside

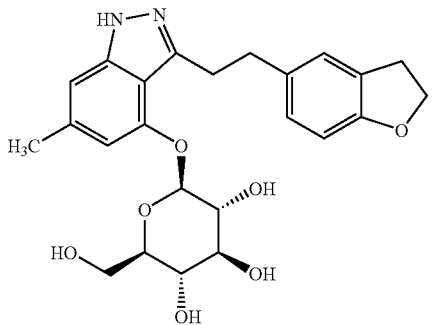

A. 1-(2,6-Bis-benzyloxy-4-methyl-phenyl)-ethanone: A mixture of 1-(2,6-dihydroxy-4-methyl-phenyl)-ethanone (0.83 g, 5.0 mmol, Tsujihara et. al. Med. Chem. 1999, 42, 5311), benzyl bromide (3.42 g, 20 mmol) and potassium carbonate (6.9 g, 50 mmol) in DMF (15 mL) was stirred at 80° C. for 3 h. The mixture was filtered and the filtrate was diluted with ethyl acetate. The organic layer was washed with water and brine, dried over anhydrous sodium sulfate and concentrated in vacuo. The residue was crystallized from ether/hexane to afford the titled compound (1.56 g, 90%) as an off-white solid.

B. 1-(2,6-Bis-benzyloxy-4-methyl-phenyl)-3-(2,3-dihydro-benzofuran-5-yl)-propenone: To a suspension of Part A (1.56 g, 4.5 mmol) in 20 mL of ethanol was added powdered potassium hydroxide (0.5 g, 9 mmol), and the mixture was stirred at room temperature for 10 min. 2,3-Dihydro-benzofuran-5-carbaldehyde (1.66 g, 11 mmol) was added, and the mixture was stirred at room temperature. When TLC showed no remaining ketone (48 h), water was added to quench the reaction. The precipitated solid was collected by filtration, washed with water, dried and recrystallized from ethanol/ether to give the titled compound (1.80 g, 84%) as yellow crystals.

C. 3-(2,3-Dihydro-benzofuran-5-yl)-1-(2,6-dihydroxy-4-methyl-phenyl)-propan-1-one: A solution of Part C (1.80 g, 3.78 mmol) in ethanol (20 mL) and ethyl acetate (20 mL) was hydrogenated over 10% Pd—C (0.5 g) under H2 (40 psi) for 4 h. The catalyst was removed by filtration and the filtrate was concentrated in vacuo. The residue was crystallized from ether/hexane to give the titled compound (1.11 g, 98%) as a white solid.

D. 3-[2-(2,3-Dihydro-benzofuran-5-yl)-ethyl]-6-methyl-1H-indazol-4-ol: To a solution of Part C (0.30 g, 1 mmol) in ethylene glycol (2 mL) was added hydrazine (0.064 g, 2 mmol). The reaction mixture was stirred for 20 min at room temperature, then heated to 160° C. for 2 h. The solution was allowed to cool to room temperature, and it was poured into water (10 mL). The pH was adjusted to pH 7 by addition of acetic acid, and the mixture was extracted with ethyl acetate. The organics were washed with brine, dried over anhydrous sodium sulfate and concentrated in vacuo. The residue was crystallized from ether/hexane to give the titled compound (0.19 g, 65%) as an off-white solid.

E. 2-{3-[2-(2,3-Dihydro-benzofuran-5-yl)-ethyl]-6-methyl-1H-indazol-4-yloxy}β-D-glucopyranoside and 2-{3-[2-(2,3-Dihydro-benzofuran-5-yl)-ethyl]-6-methyl-1H-indazol-4-yloxy}-6-O-acetyl-β-D-glucopyranoside: To a solution of Part D (0.15 g, 0.5 mmol) in acetone (1 mL) was added potassium carbonate (0.35 g, 2.5 mmol), followed by addition of 2,3,4,6-tetra-O-acetyl-α-D-glucopyranosyl bromide (0.41 g, 1 mmol). The reaction mixture was stirred at room temperature for 24 h. Then solids were filtered and washed with ethyl acetate. The ethyl acetate solution was washed with water and brine, dried over anhydrous sodium sulfate and concentrated in vacuo. The residue was dissolved in methanol (2 mL) and chloroform (0.5 mL), followed by addition of excess of potassium carbonate. The resulting mixture was stirred at room temperature overnight. Then solids were filtered and washed with ethyl acetate. The ethyl acetate solution was washed with water and brine, dried over anhydrous sodium sulfate and concentrated in vacuo. The product was purified by chromatography on silica gel:eluting with methanol/chloroform (5:100) to give the title compound (0.010 g, yield: 4%, by-product) as an off-white solid; eluting with methanol/chloroform (10:100) to give the title compound (0.096 g, yield: 42%) as a white solid. $^1$HNMR (300 MHz, CD$_3$OD) δ 7.11 (s, 1H), 6.95 (d, J=8.23 Hz, 1H), 6.86 (s, 1H), 6.61-6.58 (m, 2H), 5.22 (d, J=7.66 Hz, 1H), 4.48 (t, J=8.69 Hz, 2H), 3.95-3.90 (m, 1H), 3.74-3.68 (m, 1H), 3.64-3.59 (m, 1H), 3.55-49 (m, 2H), 3.45-3.36 (m, 2H), 3.21-3.13 (m, 3H), 3.03-2.97 (m, 2H), 2.43 (s, 3H). MS: m/z (MH$^+$) 457.

Example 2

2-{3-[2-(2,3-Dihydro-benzofuran-5-yl)-ethyl]-6-methyl-1H-indazol-4-yloxy}-6-O—acetyl-β-D-glucopyranoside

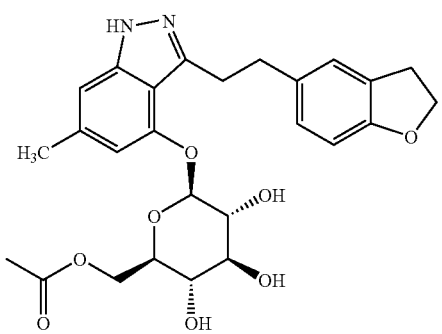

The title compound was isolated as a by-product in Example 1, Part E. ¹HNMR (300 MHz, CD₃OD) δ 7.08 (s, 1H), 6.95-6.92 (m, 1H), 6.87 (s, 1H), 6.58 (d, J=6.67 Hz, 2H), 5.19 (d, J=7.66 Hz, 1H), 4.46 (t, J=8.67 Hz, 2H), 4.43-4.38 (m, 1H), 4.23-4.18 (m, 1H), 3.69-3.58 (m, 2H), 3.54-3.42 (m, 3H), 3.16-3.11 (m, 3H), 3.01-2.96 (m, 2H), 2.42 (s, 3H), 1.93 (s, 3H). MS: m/z (MH⁺) 499.

Example 3

2-{3-[2-(2,3-Dihydro-benzo[1,4]dioxin-6-yl)-ethyl]-6-methyl-1H-indazol-4-yloxy}β-D-glucopyranoside

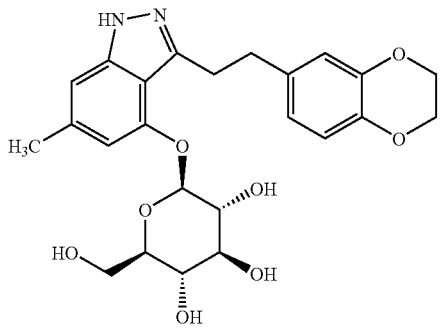

The title compound was prepared from 1-(2,6-bis-benzyloxy-4-methyl-phenyl)-ethanone and 2,3-dihydro-benzo[1,4]dioxine-6-carbaldehyde by the same procedure as described in Example 1. ¹HNMR (300 MHz, CD₃OD) δ 6.85 (s, 1H), 6.71-6.67 (m, 3H), 6.59 (s, 1H), 5.20 (d, J=7.51 Hz, 1H), 4.17 (s, 4H), 4.12-4.07, (m, 1H), 3.93-3.88 (m, 1H), 3.72-3.66 (m, 1H), 3.62-3.56 (m, 1H), 3.52-3.47 (m, 2H), 3.41-3.36 (m, 1H), 3.22-3.16 (m, 1H), 2.98-2.92 (m, 2H), 2.41 (s, 3H). MS: m/z (MH⁺) 473.

Example 4

2-[6-Methyl-3-(2-naphthalen-2-yl-ethyl)-1H-indazol-4-yloxy]-β-D-glucopyranoside

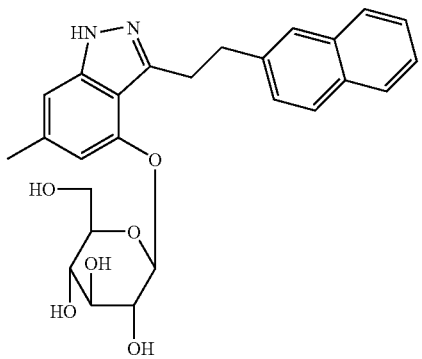

The title compound was prepared from 1-(2,6-bis-benzyloxy-4-methyl-phenyl)-ethanone and 2-Naphthaldehyde by the same procedure as described in Example 1. ¹HNMR (400 MHz, CD₃OD) δ 7.78 (m, 3H), 7.72 (s, 1H), 7.45-7.39 (m, 3H), 6.89 (s, 1H), 6.65 (s, 1H), 5.27 (d, J=7.9 Hz, 1H), 3.93 (d, J=10.0 Hz, 1H), 3.76-3.66 (m, 2H), 3.58-3.53 (m, 4H), 3.48-3.32 (m, 3H), 2.45 (s, 3H). MS: m/z (MH⁺) 465.

Example 5

2-{6-Methyl-3-[2-(5,6,7,8-tetrahydro-naphthalen-2-yl)-ethyl]-1H-indazol-4-yloxy}-β-D-glucopyranoside

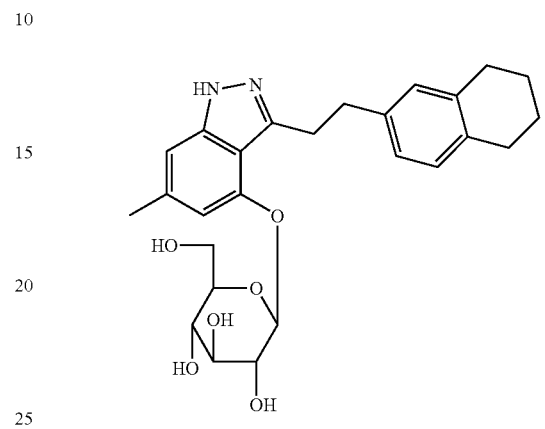

The intermediate, 1-(2,6-bis-benzyloxy-4-methyl-phenyl)-ethanone, was treated with 2-naphthaldehyde as described in Example 1, Part B. Subsequent catalytic hydrogenation as described in Example 1, Part C, provided 1-(2,6-Dihydroxy-4-methyl-phenyl)-3-(5,6,7,8-tetrahydro-naphthalen-2-yl)-propan-1-one as a by-product. Further treatment of this by-product as described in Example 1, Part D and E, afforded the title compound. ¹HNMR (400 MHz, CD₃OD) δ 7.02 (s, 1H), 6.93 (m, 2H), 6.87 (s, 1H) 6.61 (s, 1H), 5.24 (d, J=7.73 Hz, 1H), 3.94 (d, J=12.05 Hz, 1H), 3.75-3.34 (m, 5H), 3.25-2.72 (m, 8H), 2.43 (s, 3H), 1.81-1.77 (m, 4H). MS: m/z (MH⁺) 469.

Example 6

2-{3-[2-(6-Methoxy-naphthalen-2-yl)-ethyl]-6-methyl-1H-indazol-4-yloxy}-β-D-glucopyranoside

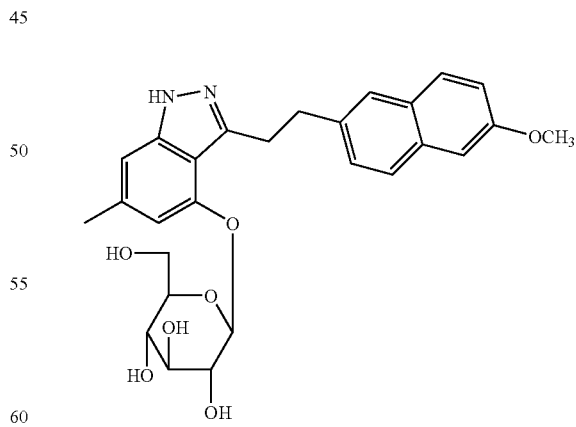

The title compound was prepared from 1-(2,6-bis-benzyloxy-4-methyl-phenyl)-ethanone and 6-methoxynaphthalene-2-carbaldehyde by the same procedure as described in Example 1. ¹HNMR (300 MHz, CD₃COCD₃) δ 7.75-7.7 (m, 3H), 7.5-7.45 (1H), 7.25-7.2 (m, 1H), 6.9 (s, 1H), 6.6 (s, 1H), 5.77

(d, J=7 Hz, 1H), 3.89 (s, 3H), 3.75-3.7 (m, 2H), 3.65-3.55 (m, 3H), 3.5-3.1 (m, 4H), 2.39 (s, 3H). MS: m/z (MH$^+$) 495.

Example 7

2-{3-[2-(6-Methoxy-5,6,7,8-tetrahydro-naphthalen-2-yl)-ethyl]-6-methyl-1H-indazol-4-yloxy}β-D-glucopyranoside

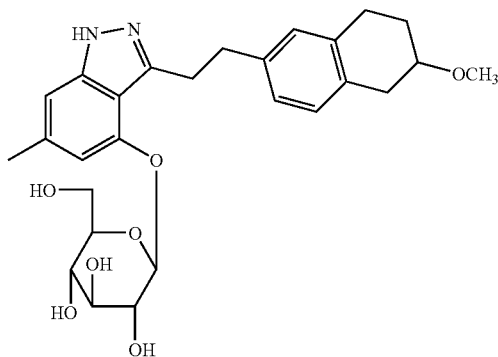

Intermediate 1-(2,6-bis-benzyloxy-4-methyl-phenyl)-ethanone, was treated with 6-methoxynaphthalene-2-carbaldehyde as described in Example 1, Part B. Subsequent catalytic hydrogenation as described in Example 1, Part C, provided 1-(2,6-dihydroxy-4-methyl-phenyl)-3-(6-methoxy-5,6,7,8-tetrahydro-naphthalen-2-yl)-propan-1-one as a by-product. Further treatment of this by-product as described in Example 1, Part D and E, afforded the title compound. $^1$HNMR (300 MHz, CD$_3$COCD$_3$) δ 7.2-7.0 (m, 2H), 6.95-6.85 (m 3H), 6.6 (s, 1H), 5.6 (s, 1H), 5.27 (d, J=7 Hz, 1H), 3.95-3.85 (m, 1H), 3.75-3.55 (m, 6H), 3.37 (s, 3H), 3.3-3.2 (m, 1H), 3.1-2.6 (m, 8H), 2.05 (s, 3H). MS: m/z (MH$^+$) 499.

Example 8

2-{3-[2-(6-Methoxy-1,2,3,4-tetrahydro-naphthalen-2-yl)-ethyl]-6-methyl-1H-indazol-4-yloxy}-β-D-glucopyranoside

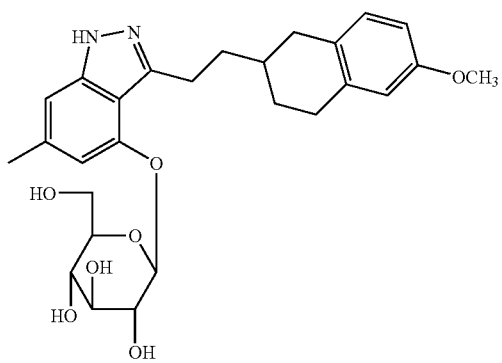

Intermediate 1-(2,6-bis-benzyloxy-4-methyl-phenyl)-ethanone, was treated with 6-methoxynaphthalene-2-carbaldehyde as described in Part B of Example 1. Subsequent catalytic hydrogenation as described in Part C of Example 1 provided 1-(2,6-dihydroxy-4-methyl-phenyl)-3-(6-methoxy-1,2,3,4-tetrahydro-naphthalen-2-yl)-propan-1-one as a by-product. Further treatment of this by-product as described in Example 1, Parts D and E, afforded the title compound. $^1$HNMR (300 MHz, CD$_3$COCD$_3$) δ 11.5 (br s, 1H), 7.05-6.95 (m, 1H), 6.87 (s, 1H), 6.65-6.6 (m, 2H), 6.57 (s, 1H), 5.21 (d, J=7 Hz, 1H), 4.5-2.25 (m, 2H), 3.95-3.85 (m, 1H), 3.72 (s, 3H), 3.7-3.55 (m, 6H), 3.3-3.05 (m, 2H), 3.0-2.75 (m, 3H), 2.37 (s, 3H), 1.95-1.7 (m, 2H), 1.5-1.35 (m, 1H). MS: m/z (MH$^+$) 499.

Example 9

2-{3-[2-(4-Methoxy-phenyl)-ethyl]-6-methyl-1H-indazol-4-yloxy}β-D-glucopyranoside

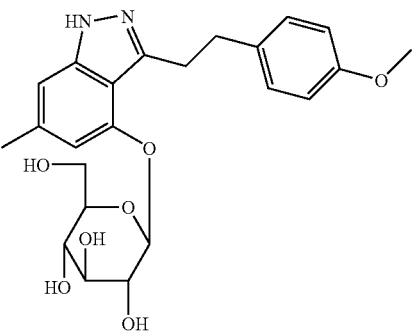

The title compound was prepared from 1-(2,6-bis-benzyloxy-4-methyl-phenyl)-ethanone and 4-methoxy-benzaldehyde by the same procedure as described in Example 1. $^1$HNMR (300 MHz, CD3OD) δ 7.18 (s, 1H), 7.15 (s, 1H), 6.86 (s, 1H), 6.82 (s, 1H), 6.80 (s, 1H), 6.61 (s, 1H), 5.23 (d, J=7.78 Hz, 1H), 3.92 (dd, J=1.79, 10.04 Hz, 1H), 3.75 (s, 3H), 3.72-3.35 (m, 6H), 3.25-3.15 (m, 1H), 3.10-2.94 (m, 2H), 2.43 (s, 3H). MS: m/z (MH$^+$) 445.

Example 10

2-{3-[2-(4-Ethoxy-phenyl)-ethyl]-6-methyl-1H-indazol-4-yloxy}β-D-glucopyranoside

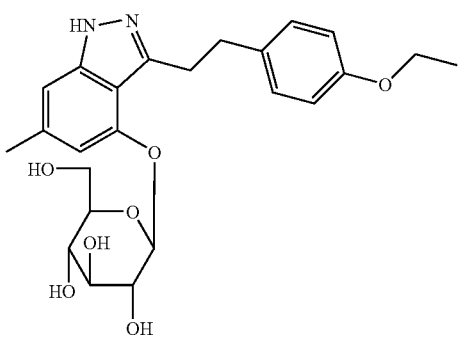

The title compound was prepared from 1-(2,6-bis-benzyloxy-4-methyl-phenyl)-ethanone and 4-ethoxy-benzaldehyde by the same procedure as described in Example 1. $^1$HNMR (300 MHz, CD3OD) δ 7.16 (s, 1H), 7.14 (s, 1H), 6.86 (s, 1H), 6.81 (s, 1H), 6.78 (s, 1H), 6.61 (s, 1H), 5.23 (d, J=7.67 Hz, 1H), 3.99 (q, J=7.10, 7.01 Hz, 2H), 3.95-3.90 (m, 1H), 3.72 (dd, J=5.62, 6.42 Hz, 1H), 3.65-3.35 (m, 7H), 3.25-3.15 (m, 1H), 3.10-2.96 (m, 2H), 2.53 (s, 3H), 1.36 (t, J=6.96 Hz, 3H). MS: m/z (MH$^+$) 459.

Example 11

2-{3-[2-(4-Chloro-phenyl)-ethyl]-6-methyl-1H-indazol-4-yloxy}-β-D-glucopyranoside

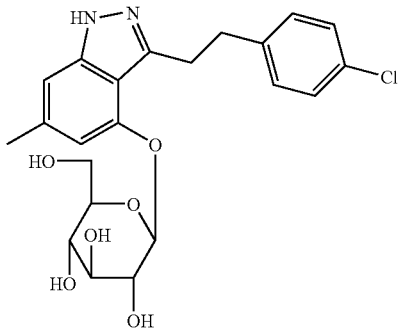

The title compound was prepared from 1-(2,6-bis-benzyloxy-4-methyl-phenyl)-ethanone and 4-chlorobenzaldehyde by the same procedure as described in Example 1. $^1$HNMR (300 MHz, CD3OD) δ 7.22 (s, 4H), 6.86 (s, 1H), 6.62 (s, 1H), 5.23 (d, J=7.48 Hz, 1H), 3.93 (dd, J=1.95, 10.16 Hz, 1H), 3.72 (dd, J=5.69, 6.40 Hz, 1H), 3.64-3.35 (m, 6H), 3.26-3.03 (m, 3H), 2.43 (s, 3H). MS: m/z (MH$^+$) 449.

Example 12

2-{3-[2-(4-Trifluoromethyl-phenyl)-ethyl]-6-methyl-1H-indazol-4-yloxy}β-D-glucopyranoside

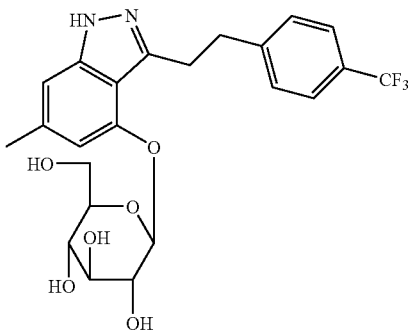

The title compound was prepared from 1-(2,6-bis-benzyloxy-4-methyl-phenyl)-ethanone and 4-trifluoromethyl-benzaldehyde by the same procedure as described in Example 1. $^1$HNMR (400 MHz, CD$_3$OD) δ 7.56 (d, J=8.09 Hz, 2H), 7.45 (d, J=8.09 Hz, 2H), 6.90 (s, 1H), 6.66 (s, 1H), 5.26 (d, J=7.7 Hz, 1H), 3.95 (d, J=10.09 Hz, 1H), 3.75 (m, 1H), 3.63-3.45 (m, 5H), 3.31-3.20 (m, 3H), 2.44 (s, 3H). MS: m/z (MH$^+$) 483.

Example 13

2-[3-(2-Benzofuran-5-yl-ethyl)-6-methyl-1H-indazol-4-yloxy]-β-D-glucopyranoside

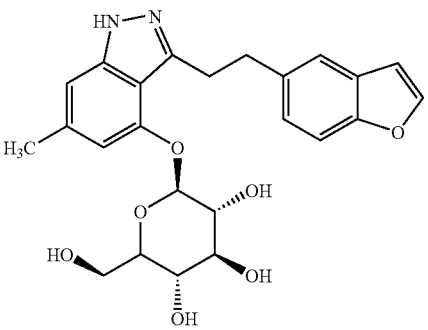

A. 1-(2-Hydroxy-6-methoxymethoxy-4-methyl-phenyl)-ethanone: A mixture of 1-(2,6-dihydroxy-4-methyl-phenyl)-ethanone (11.65 g, 70 mmol), bromomethyl methyl ether (17.5 g, 140 mmol) and potassium carbonate (48 g, 350 mmol) in acetonitrile (280 mL) was stirred at room temperature overnight. The mixture was filtered and the filtrate was diluted with ethyl acetate. The organic layer was washed with water and brine, dried over anhydrous sodium sulfate and concentrated in vacuo. The crude product was purified by chromatography on silica gel eluting with ethyl acetate/hexane (10:100) to yield the title compound (13.1 g, yield: 89%) as yellow oil.

B. 3-Benzofuran-5-yl-1-(2-hydroxy-6-methoxymethoxy-4-methyl-phenyl)-propan-1-one: A 50% aqueous potassium hydroxide solution (6 mL) was added to a solution of Part A (1.26 g, 6 mmol) in ethanol (30 mL), and the mixture was stirred at room temperature for 10 min. Then 5-benzofurancarboxaldehyde (0.95 g, 6.5 mmol, Humphrey, Guy R., U.S. Pat. No. 5,149,838, 1992) was added, and the mixture was stirred at room temperature overnight. 4-(Dimethylamino)pyridine (0.73 g, 6 mmol) was added to the reaction mixture containing the chalcone, and the mixture was hydrogenated over 10% Pd—C (0.35 g) under 30 psi for 4 h. The catalysts were removed by filtration, the filtrate was neutralized with 10% aqueous HCl and extracted with ethyl acetate. The organic layer was washed with water and brine, dried over anhydrous sodium sulfate and concentrated in vacuo. The residue was crystallized from ethanol to give the titled compound (1.23 g, 60%) as a white solid.

C. 3-Benzofuran-5-yl-1-(2,6-dihydroxy-4-methyl-phenyl)-propan-1-one: To a solution of Part B (1.23 g, 3.6 mmol) in dioxane (12 mL) and isopropanol (6 mL) was added dropwise concentrated HCl (1.5 mL). The reaction mixture was stirred at room temperature for 4 h, quenched with water and extracted with ethyl acetate. The organic extracts were washed with brine, dried over anhydrous sodium sulfate and concentrated in vacuo. The crude product was purified by chromatography on silica gel eluting with ethyl acetate/hexane (50:50) to give the titled compound (0.46 g, yield: 46%) as a yellow solid.

D. 2-[3-(2-Benzofuran-5-yl-ethyl)-6-methyl-1H-indazol-4-yloxy]-β-D-glucopyranoside: The title compounds were prepared from Part C by the same procedure as described in Example 1, Part D and E. $^1$HNMR (300 MHz, CD$_3$OD) δ 7.69

(d, J=1.98 Hz, 1H), 7.51 (s, 1H), 7.37 (d, J=8.62 Hz, 1H), 7.22 (dd, J=1.23, 8.35 Hz, 1H), 6.89 (s, 1H), 6.79-6.78 (m, 1H), 6.65 (s, 1H), 5.26 (d, J=7.67 Hz, 1H), 3.97-3.93 (m, 1H), 3.76-3.64 (m, 2H), 3.62-3.52 (m, 3H), 3.50-3.43 (m, 2H), 3.27-3.17 (m, 2H), 2.46 (s, 3H). MS: m/z (MH$^+$) 455.

Example 14

2-[3-(2-Benzofuran-5-yl-ethyl)-6-methyl-1H-indazol-4-yloxy]-6-O-acetyl-β-D-glucopyranoside

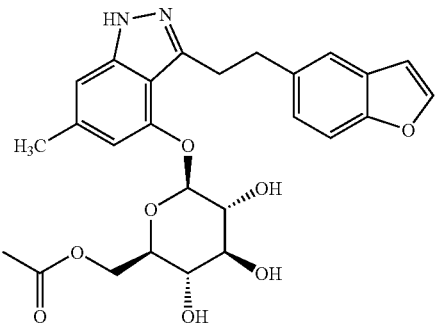

The title compound was isolated as a by-product in Example 13, Part D. $^1$HNMR (300 MHz, CD$_3$OD) δ 7.66 (d, J=2.38 Hz, 1H), 7.48 (s, 1H), 7.37 (d, J=8.28 Hz, 1H), 7.20 (d, J=8.45 Hz, 1H), 6.90 (s, 1H), 6.77-6.75 (m, 1H), 6.60 (s, 1H), 5.23 (d, J=7.76 Hz, 1H), 4.45-4.40 (m, 1H), 4.25-4.19 (m, 1H), 3.75-3.63 (m, 2H), 3.59-3.42 (m, 3H), 3.25-3.15 (m, 3H), 2.45 (s, 3H), 1.93 (s, 3H). MS: m/z (MH$^+$) 497.

Example 15

2-{3-[2-(2,3-Dihydro-benzofuran-5-yl)-ethyl]-1,6-dimethyl-1H-indazol-4-yloxy}-β-D-glucopyranoside

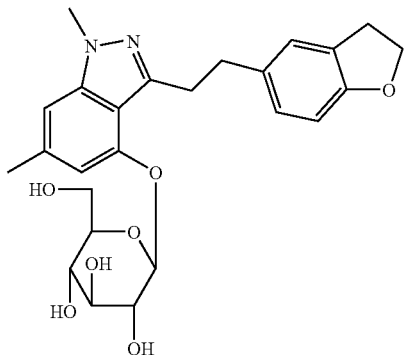

A. 3-[2-(2,3-Dihydro-benzofuran-5-yl)-ethyl]-1,6-dimethyl-1H-indazol-4-ol: To a solution of 3-(2,3-dihydro-benzofuran-5-yl)-1-(2,6-dihydroxy-4-methyl-phenyl)-propan-1-one (0.30 g, 1 mmol, prepared as the same procedure in Example 1, Part C) in ethylene glycol (2 mL) was added methyl hydrazine (0.092 g, 2 mmol). The reaction mixture was stirred for 20 min at room temperature, then heated to 160° C. for 2 h. The solution was allowed to cool to room temperature, and it was poured into water (50 mL). The pH was adjusted to 7 by addition of acetic acid, and the mixture was extracted with ethyl acetate. The organics were washed with brine, dried over anhydrous sodium sulfate and concentrated in vacuo. The residue was crystallized from ether/hexane to give the titled compound (0.12 g, 40%) as an off-white solid.

B. 2-{3-[2-(2,3-Dihydro-benzofuran-5-yl)-ethyl]-1,6-dimethyl-1H-indazol-4-yloxy}-β-D-glucopyranoside: The title compound was prepared from Part D by the same procedure described in Example 1, Part E. $^1$HNMR (300 MHz, CD$_3$OD) δ 7.10 (s, 1H), 6.94 (d, J=8.09 Hz, 1H), 6.85 (s, 1H), 6.85-6.61 (m, 1H), 6.58 (s, 1H), 5.22 (d, J=7.64 Hz, 1H), 4.48 (t, J=8.69 Hz, 2H), 3.92 (dd, J=2.08, 9.98 Hz, 1H), 3.86 (s, 1H), 3.71 (dd, J=5.6888, 6.34 Hz, 1H), 3.64-3.38 (m, 6H), 3.34-3.30 (m, 1H), 3.21-3.04 (m, 3H), 3.01-2.93 (m, 2H), 2.45 (s, 3H). MS: m/z (MH$^+$) 471.

Example 16

2-{3-[2-(4-Methanesulfonylamino-phenyl)-ethyl]-6-methyl-1H-indazol-4-yloxy}β-D-glucopyranoside

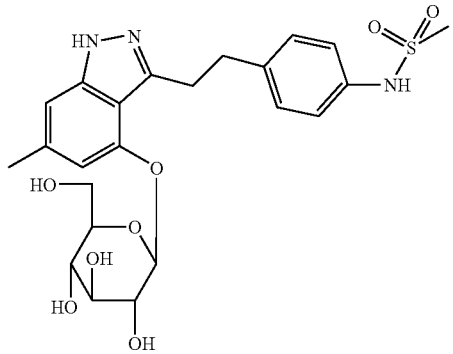

A. 3-(4-Amino-phenyl)-1-(2,6-bis-benzyloxy-4-methyl-phenyl)-propenone: A mixture of 1-(2,6-bisbenzyloxy-4-methyl-phenyl)-ethanone (1.2 g, 3.5 mmol), prepared as described in Part A of Example 1, and powdered potassium hydroxide (0.4 g, 6.9 mmol) in ethanol (20 mL) was treated as described in Part B of Example 1 to provide the product as a solid. The solids (1.1 g, 2.24 mmol) were suspended in methanol (25 mL) and treated with concentrated hydrochloric acid (1.5 mL). The mixture was stirred at reflux for forty minutes, cooled to room temperature (RT) and a saturated sodium bicarbonate solution was slowly added. The methanol was removed under reduced pressure and the aqueous mixture extracted with ethyl acetate (2×60 mL). The combined ethyl acetate extract was washed with brine, dried over MgSO$_4$, filtered and concentrated in vacuo to afford the title compound as a semi-solid (0.892 g, 89%).

B. N-{4-[3-(2,6-Bis-benzyloxy-4-methyl-phenyl)-3-oxo-propenyl]-phenyl}-methanesulfonamide: Methanesulfonyl chloride (0.16 mL, 2.1 mmol) was added dropwise to a cold (0° C.) mixture of the compound prepared in Part A and triethylamine (0.69 mL, 5 mmol) in methylene chloride (30 mL). The resulting homogenous mixture was stirred at 0° C. for one hour then warmed up to RT. After an addition thirty minutes at RT ice water (30 mL) was added and the layers separated. The organic extract was washed with 0.5 M HCl solution (1×30 mL) then H$_2$O (1×30 mL) and dried over MgSO$_4$. The mixture was filtered and concentrated in vacuo to provide the title compound (0.98 g, 94%).

C. 2-{3-[2-(4-Methanesulfonylamino-phenyl)-ethyl]-6-methyl-1H-indazol-4-yloxy}β-D-glucopyranoside: The compound prepared in Part B was treated as described in Example 1, Parts C, D and E, to provide the title compound as an off-white solid. ¹HNMR (300 MHz, CD₃OD) δ 7.23 (d, J=8.48 Hz, 2H), 7.13 (d, J=8.36 Hz, 2H), 6.86 (s, 1H), 6.61 (s, 1H), 7.20 (d, J=7.51 Hz, 1H), 3.95-3.91 (m, 1H), 3.74-3.37 (m, 5H), 3.26-3.05 (m, 4H), 2.90 (s, 3H), 2.43 (s, 3H). MS: m/z (MH⁺) 508.

Example 17

2-[3-(2-Cyclohexyl-ethyl)-6-methyl-1H-indazol-4-yloxy]-β-D-glucopyranoside

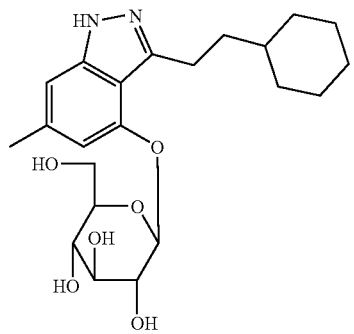

A. 1-(2,6-Bis-benzyloxy-4-methyl-phenyl)-3-cyclohex-1-enyl-propenone: Lithium diisopropylamide (1.5 mL, 1.5 mmol, 2M solution in heptane/tetrahydrofuran/ethylbenzene) was slowly added to a cold (−78° C.) solution of 1-(2,6-Bis-benzyloxy-4-methyl-phenyl)-ethanone prepared in Part A of Example 1 in dry THF (10 mL). The mixture was stirred at −78° C. with slow warming to 0° C. over a 60 minute period then re-cooled to −30° C. and 1-cyclohexene-1-carboxaldehyde (256 mg, 2.3 mmol) was added dropwise. After three hours at room temperature, the mixture was cooled in an ice bath and quenched with saturated ammonium chloride (5 mL). Water (50 mL) was added and the mixture extracted with ethyl acetate (2×60 mL). The combined ethyl acetate extracts was washed with brine, dried over MgSO₄, filtered, evaporated in vacuo and purified by column chromatography to provide the title compound (0.166 g, 51% based on recovered starting material).

B. 3-Cyclohexyl-1-(2,6-dihydroxy-4-methyl-phenyl)-propan-1-one: A solution of the compound (0.16 g, 0.37 mmol) prepared in Part A in a mixture of ethanol and ethyl acetate (1:1) was hydrogenated over a catalytic amount of 10% Pd—C in a Parr apparatus at 15 psi of hydrogen pressure for 24 hours. The mixture was filtered through CELITE™ and evaporated in vacuo to afford the title compound (0.093 g, 97%).

C. 2-[3-(2-Cyclohexyl-ethyl)-6-methyl-1H-indazol-4-yloxy]-β-D-glucopyranoside: The compound obtained in Part B was treated as described in Example 1, Part D and E, to provide the title compound as an off-white solid. ¹HNMR (400 MHz, CD₃OD) δ 6.85 (s, 1H), 6.58 (s, 1H), 5.2 (d, J=7.36 Hz, 1H), 3.92 (d, J=11.91 Hz, 1H), 3.69-3 (m, 1H), 3.49-3.60 (m, 2H), 3.38-3.43 (m, 1H), 3.18-3.20 (m, 1H), 2.96-2.98 (m, 1H), 2.43 (s, 3H), 1.82-1.88 (m, 2H), 1.61-1.74 (m, 6H), 1.33-1.35 (m, 5H), 1.24-1.30 (m, 2H). MS: m/z (MH⁺) 421.

Example 18

2-[3-(2-Benzofuran-5-yl-ethyl)-1H-indazol-4-yloxy]-β-D-glucopyranoside

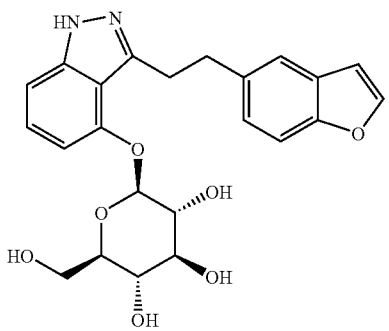

The title compound was prepared from 1-(2,6-dihydroxyphenyl)-ethanone and 5-benzofuran carboxaldehyde by the same procedure as described in Example 13. ¹HNMR (300 MHz, CD₃OD) δ 7.67 (d, J=2.2 Hz, 1H), 7.49 (s, 1H), 7.37 (d, J=8.42 Hz, 1H), 7.29 (d, J=8.11 Hz, 1H), 7.25-7.19 (m, 1H), 7.08 (d, J=8.3 Hz, 1H), 6.78-6.75 (m, 2H), 5.26 (d, J=7.71 Hz, 1H), 3.92 (dd, J=11.79, 1.88 Hz, 1H), 3.75-3.63 (m, 1H), 3.62-3.54 (m, 3H), 3.53-3.45 (m, 3H), 3.26-3.18 (m, 2H). MS: m/z (MH⁺) 441.

Example 19

2-{3-[2-(2,3-Dihydro-benzofuran-5-yl)-ethyl]-6-ethyl-1H-indazol-4-yloxy}-D-glucopyranoside

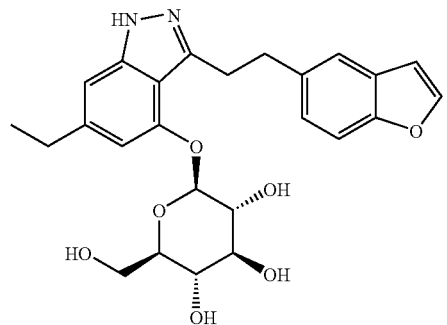

A. 1-(2,6-Dihydroxy-4-ethyl-phenyl)-ethanone: A solution of 1,3-diacetoxyacetophenone (3.2 g, 13.5 mmol) in acetic acid (30 mL) was hydrogenated over 10% Pd—C (3.0 g) under H₂ (50 psi) overnight. The catalyst was removed by filtration and the filtrate was concentrated in vacuo. The resulting crude product (1,3-diacetoxy-5-ethylbenzene) was used directly in the next step.

To a suspension of AlCl₃ (5.4 g, 40.6 mmol) in chlorobenzene (15 mL) was added dropwise a solution of 1,3-diacetoxy-5-ethylbenzene (3.0 g, 13.5 mmol) at 90° C. over the period of 30 min. The reaction mixture was stirred at 90° C. for 1 h and then poured into ice-10% HCl (50 mL please clarify). The aqueous layer was extracted with ethyl acetate. The organic layer was washed with water and brine, dried over anhydrous sodium sulfate and concentrated in vacuo. The residue was crystallized from ether/hexane to give the title compound (1.5 g, 62%) as a white solid.

B. 2-{3-[2-(2,3-Dihydro-benzofuran-5-yl)-ethyl]-6-ethyl-1H-indazol-4-yloxy}-β-D-glucopyranoside: The title compound was prepared from Part A and 2,3-dihydro-benzofuran-5-carbaldehyde by the same procedure as described in Example 1. $^1$HNMR (300 MHz, CD$_3$OD) δ 7.10 (s, 1H), 6.95 (d, J=7.90 Hz, 1H), 6.88 (s, 1H), 6.64 (s, 1H), 6.60 (d, J=8.11 Hz, 1H), 5.24 (d, J=7.38 Hz, 1H), 4.48 (t, J=8.69 Hz, 2H), 3.93 (dd, J=1.92, 9.97 Hz, 1H), 3.72 (dd, J=5.75, 6.58 Hz, 1H), 3.66-3.35 (m, 6H), 3.25-3.19 (m, 1H), 3.15 (t, J=8.62 Hz, 2H), 3.08-2.92 (m, 2H), 2.72 (q, J=7.54, 7.57 Hz, 2H), 1.29 (t, J=7.47 Hz, 3H). MS: m/z (MH$^+$) 471.

Example 20

2-[3-(4-Methoxy-phenylsulfanylmethyl)-1H-indazol-4-yloxy]-β-D-glucopyranoside

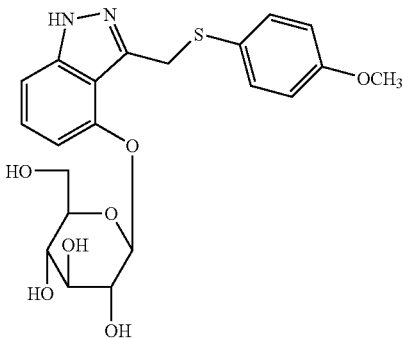

A. 1-[4-(tert-Butyl-dimethyl-silanyloxy)-3-methyl-indazol-1-yl]-ethanone: To a solution of 4-(tert-Butyl-dimethylsilanyloxy)-3-methyl-1H-indazole (200 mg, 0.76 mmol), prepared according to Boehm et. al. J. Med. Chem., 2000, 43, 2664-2674, in DMF (3 mL) at room temperature was added potassium carbonate (516 mg, 3.80 mmol) followed by acetic anhydride (143 l, 1.52 mmol) and the resulting reaction mixture was allowed to stir at room temperature for 2 h. The reaction mixture was poured onto water and extracted with ethyl acetate. The combined ethyl acetate extracts were dried over anhydrous sodium sulfate and concentrated in vacuo. Chromatography (SiO$_2$, 20% Ethyl Acetate-Hexanes eluant) provided 200 mg of the desired product as an off-white solid. (231 mg, 87% yield).

B. 1-[3-Bromomethyl-4-(tert-butyl-dimethyl-silanyoxy)-indazol-1-yl]-ethanone: To a solution of the acetyl compound prepared in the previous step (1.9 g, 6.25 mmol), in carbon tetrachloride at room temperature was added AIBN (205 mg, 1.25 mmol) and NBS (1.45 g, 8.13 mmol). The resulting reaction mixture was allowed to stir at reflux for 1 h then cooled to room temperature and stirred for an additional 18 h. The reaction mixture was concentrated in vacuo. Chromatography (SiO$_2$, 5% Ethyl Acetate-Hexanes eluant) provided the desired bromide as dark red oil in quantitative yields.

C. 1-[4-(tert-Butyl-dimethyl-silanyloxy)-3-(4-methoxy-phenylsulfanylmethyl)-indazol-1-yl]-ethanone: To a solution of the bromide prepared in the previous step (0.2 g, 0.522 mmol), in methylene chloride at room temperature was added triethylamine (0.055 g, 0.548 mmol) and 4-methoxy-benzenethiol (0.077 g, 0.548 mmol) and the resulting mixture was stirred at room temperature for 4 h. The reaction mixture was diluted with methylene chloride and washed with water, brine, dried over magnesium sulfate, filtered and concentrated in vacuo. Chromatography (SiO$_2$, 5% ethyl acetate:hexane eluent) provided 0.2 g of the desired product as an off-white solid (0.23 g, 85% yield).

D. 1-[4-Hydroxy-3-(4-methoxy-phenylsulfanylmethyl)-indazol-1-yl]-ethanone: To a solution of the compound prepared in part C (0.2 g, 0.452 mmol), in DMF at room temperature was added potassium fluoride (0.053 g, 0.905 mmol) and 48% aqueous hydrogen bromide (0.03 mL, 0.136 mmol) and the resulting mixture was allowed to stir at room temperature for 5 days. The reaction solution was poured into a saturated sodium bicarbonate solution and extracted with ethyl acetate/hexane (3:1). The combined ethyl acetate extracts were washed with water, brine, dried over MgSO$_4$, filtered and concentrated in vacuo. Chromatography (SiO$_2$, 10% ethyl acetate:hexane eluent) provided the title compound (0.076 g, 50%) as an off-white solid.

E. 2-[1-Acetyl-3-(4-methoxy-phenylsulfanylmethyl)-1H-indazol-4-yloxy]-β-D-glucopyranoside: To a solution of the hydroxyl compound prepared in part D (0.076 g, 0.244 mmol) in acetone at room temperature was added potassium carbonate (0.085 g, 0.61 mmol) and 2,3,4,6-tetra-O-acetyl-α-D-glucopyranosyl bromide (0.15 g, 0.366 mmol) and the resulting mixture was allowed to stir at room temperature 24 h. The reaction mixture was diluted with water, the acetone was removed and the product was extracted with ethyl acetate. The combined ethyl acetate extracts were washed with brine, dried over MgSO$_4$, filtered and concentrated in vacuo. Chromatography (SiO$_2$, 25% ethyl acetate:hexane eluent) provided the acetylated intermediate (0.065 g, 40%) as an off-white solid. To a solution of this intermediate (0.065 g, 0.099 mmol) in methanol at room temperature was added sodium methoxide in methanol (0.1 mL, 0.463 mmol) and the resulting reaction mixture was allowed to stir at room temperature for 1 h. The reaction mixture was diluted with water, the methanol was removed and the product was extracted with ethyl acetate. The combined ethyl acetate extracts were washed with brine, dried over MgSO$_4$, filtered and concentrated in vacuo to yield the title compound (0.036 g, 80%) as an off-white solid. $^1$HNMR (300 MHz, CD$_3$OD) δ 7.30-7.25 (m, 3H), 7.07 (d, J=8.27 Hz, 1H), 6.83-6.76 (m, 3H), 5.15 (d, J=7.55 Hz, 1H), 4.61 (d, Hz, J=13.0 Hz, 1H), 4.41 (d, J=13.0 Hz, 1H), 3.96-3.91 (dd, J=1.95 Hz, J=10.05 Hz, 1H), 3.75 (s, 3H), 3.63-3.45 (m, 5H). MS: m/z (MH$^+$) 449.

Example 21

2-[3-(4-Methoxy-benzyl)-6-methyl-1H-indazol-4-yloxy]-β-D-glucopyranoside

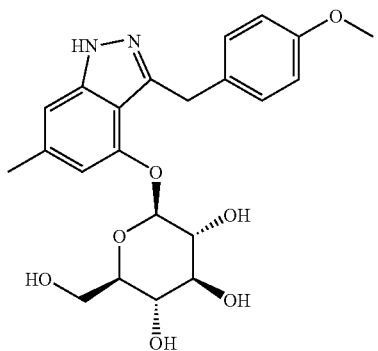

A. 1-(2,6-Dihydroxy-4-methyl-phenyl)-2-(4-methoxy-phenyl)-ethanone (NB18926-186): To a mixture of 5-methylbenzene-1,3-diol (0.37 g, 3 mmol) and (4-methoxy-phenyl)-acetic acid (0.55 g, 3 mmol) was added dropwise boron trifluoride diethyl etherate (1.5 mL, 12 mmol). The reaction mixture was heated to 100° C. and stirred for 2 h. After cooling to room temperature, the mixture poured into aqueous sodium acetate and stirred for 5 min, then extracted with ethyl acetate. The organic extracts were washed with brine, dried over anhydrous $Na_2SO_4$ and concentrated in vacuo. The crude product was purified by chromatography on silica gel: eluting with acetone/ethyl acetate/hexane (12:4:100) to provide the titled compound (0.24 g, 29%) as a yellow solid; eluting with acetone/ethyl acetate/hexane (15:5:100) to provide 1-(2,4-dihydroxy-6-methyl-phenyl)-2-(4-methoxy-phenyl)-ethanone (0.48 g, 59%) as a yellow solid.

B. 2-[3-(4-Methoxy-benzyl)-6-methyl-1H-indazol-4-yloxy]-β-D-glucopyranoside: the title compound was prepared from Part A by the same procedure as described in Example 1, Part D and Part E. $^1$HNMR (300 MHz, $CD_3OD$) δ 7.22 (d, J=8.69 Hz, 1H), 6.87 (s, 1H), 6.78 (d, J=8.57 Hz, 2H), 6.58 (s, 1H), 5.12 (d, J=7.64 Hz, 1H), 4.49 (d, J=15.12 Hz, 1H), 4.24 (d, J=15.06 Hz, 1H), 3.89 (dd, J=2.07, 12.06 Hz, 1H). 3.73 (s, 3H), 3.70-3.62 (m, 2H), 3.58-3.45 (m, 2H), 3.39 (d, J=8.71 Hz, 1H), 2.41 (s, 3H). MS: m/z ($MH^+$) 431.

Example 22

2-[3-(2,3-Dihydro-benzofuran-5-ylmethyl)-6-methyl-1H-indazol-4-yloxy]-β-D-glucopyranoside

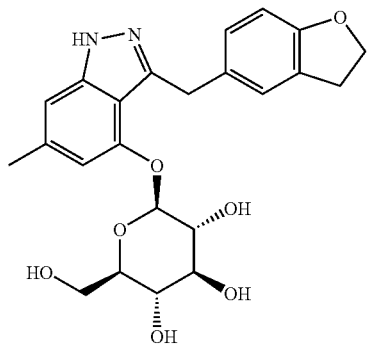

The title compound was prepared from 5-methyl-benzene-1,3-diol and (2,3-Dihydro-benzofuran-5-yl)-acetic acid by the same procedure as described in Example 16. $^1$HNMR (300 MHz, $CD_3OD$) δ 7.16 (s, 1H), 7.03 (d, J=7.80 Hz, 1H), 6.86 (s, 1H), 6.59-6.56 (m, 2H), 5.12 (d, J=7.47 Hz, 1H), 4.48-4.43 (m, 3H), 4.23 (d, J=15.07 Hz, 1H), 3.90 (dd, J=1.63, 12.03 Hz, 1H), 3.70-3.59 (m, 2H), 2.57-3.51 (m, 2H), 3.48-3.35 (m, 1H), 3.11 (d, J=8.73 Hz, 2H), 2.41 (s, 3H). MS: m/z ($MH^+$) 443.

H. BIOLOGICAL EXAMPLES

Example 1

Materials and Methods

Cloning of the human SGLT1 and human SGLT2 cDNAs and construction of the mammalian expression vector: The human SGLT1 cDNA (Genbank M24847) was cloned from human small intestine. Human SGLT2 cDNA (Genbank M95549) was cloned from human kidney. Both full cDNAs were subcloned into pcDNA and sequenced to verify the integrity of the construct.

Generation of CHO-K1 cells stably expressing human SGLT1 or human SGLT2: Transfection of CHO-K1 cells was performed using DMRIE-C reagent (Life Technologies, Gaithersburg, Md.). Transfectants were then selected in the presence of the antibiotic G418 (Gibco-BRL, Grand Island, N.Y.) at 400 µg/ml. Individual clones were then characterized using the functional assay described below.

Cell-based assay for sodium-dependent glucose transport: Cell lines stably expressing human SGLT1 or SGLT2 were then used for functional analysis of $Na^+$-dependent glucose uptake. Briefly, cells were plated at a density of 65,000 cells per well in a 96-well plate and allowed to grow for 48 hours. Cells were subsequently washed one time with Assay Buffer (50 mM HEPES pH 7.4, 20 mM Tris, 5 mM KCl, 1 mM $MgCl_2$, 1 mM $CaCl_2$ and 137 mM NaCl) and treated with compound in the absence or presence of NaCl for 15 minutes. Cells were then labeled with $^{14}$C-α-methylglucopyranoside (AMG, Sigma, St. Louis, Mo.), a non-metabolizable glucose analog specific for sodium-dependent glucose transporters as previously described (Peng, H. and Lever J. E. Post-transcriptional regulation of $Na^+$/glucose cotransporter (SGLT1) gene expression in LLC-PK1 cells. J Biol Chem 1995; 270:20536-20542.). After 2 hours the labelled cells were washed three times with ice-cold PBS. After aspiration, cells were solubilized using Microscint 20 (Packard, Meriden, Conn.) and Na-dependent $^{14}$C-AMG uptake was quantified by measuring radioactivity. Plates were counted in a TopCount (Packard, Meriden, Conn.). Results are reported as the % inhibition or IC50 value from a representative experiment. Variability for the functional assay was typically within 20%.

Example 2

In Vivo Assay for Efficacy

Male Zucker Diabetic Fatty (ZDF) rats (7-8 weeks) were obtained from Charles River. Animals were maintained on a 12-hour light/dark cycle in a temperature-controlled room. Animals were given ad libitum access to food (standard rodent diet Purina 5008) and water. Animals were fasted for 12 hours prior to initiation of the experiment. On the morning of the experiment, animals were administered vehicle (0.5% methylcellulose) or compound by oral gavage (1 ml/kg). After one hour, animals received an oral glucose challenge (4 ml/kg of 50% solution) and were immediately placed in metabolism cages. Animals were given free access to water and urine was collected for 4 hours. Urinary glucose was quantified using the Trinder Reagent (Sigma).

Example 3

Effects on Plasma Glucose, Plasma Insulin, Plasma Triglycerides, Plasma Free Fatty Acids, Liver Weight, and Body Weight To examine the effect of an SGLT inhibitor in combination with an RXR agonist, female db/db mice (6-7 weeks of age/Jackson Labs, ME) are treated daily for 11 days with vehicle (0.5% methylcellulose), an RXR agonist (0.1-10 mpk (mg/kg)), T-1095 (100 mpk), or RXR agonist plus SGLT inhibitor. Mice (n=8 animals/group) receive the test compounds or vehicle by oral gavage in a volume of 10 ml/kg of body weight. Body weight is recorded on day 1, prior to dosing, and days 4, 8 and 11. Eighteen hours after the final dose, mice are weighed and anesthetized with $CO_2/C_2$ (70:30). Mice are then bled by retro-orbital sinus puncture into 2 mL heparinized polypropylene tubes on ice. Plasma samples are then assayed for glucose, insulin, triglycerides, and free fatty acids. Livers are excised, weighed and frozen.

The SGLT inhibitors and RXR agonists have distinct mechanisms of action. Improved glycemic control, measured as a decrease in plasma glucose, plasma insulin, plasma free fatty acids, or plasma triglycerides, or a combination thereof, can be observed at lower concentrations of an RXR agonist when given in combination with an SGLT inhibitor. Therefore, a leftward shift in the dose-response curve for effect of an RXR agonist on the above parameters can become apparent. In addition, the weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. A reduction in the amount of an RXR agonist necessary to achieve efficacy in turn improves the side-effect profile. The decreased side effects can include such conditions as fatty liver, increased liver weight, body weight gain, heart weight gain, edema, cardiac hypertrophy, hepatohypertrophy, hypoglycemia, and hepatotoxicity, or any combination thereof.

Example 4

Effects on plasma Glucose, HbA1c, Hematocrit, Plasma Insulin, Plasma Triglycerides, Plasma Free Fatty Acids, Total Cholesterol, HDL, Plasma Drug Levels, Liver Weight, Heart Weight, Fat Content and Body Weight To examine the effect of an SGLT inhibitor in combination with an RXR agonist, male ZDF rats (6 weeks of age/GMI) are treated daily for 28 days with vehicle (0.5% methylcellulose), an RXR agonist (0.1 mpk-10 mpk), SGLT inhibitor (3-100 mpk), or RXR agonist plus SGLT inhibitor. Rats (n=8 animals/group) receive the test compounds or vehicle by oral gavage in a volume of 2 ml/kg of body weight. Body weight is recorded on day 1, prior to dosing, and twice a week for the duration of the study. On the day prior to the final dose, animals are fasted overnight. One hour after the final dose, rats are weighed and anesthetized with $CO_2/C_2$ (70:30). Rats are then bled by retro-orbital sinus puncture into 2 mL heparinized polypropylene tubes on ice. Rats then receive a glucose challenge (2 g/kg p.o) and are placed in metabolism cages for the urine collection (4 hours). Animals are then sacrificed and epididymal fat pads, livers, and hearts are excised, weighed and frozen for histological examination. Plasma samples are then assayed for glucose, HbA1c, insulin, hematocrit, plasma drug levels, total cholesterol, HDL, free fatty acids, and triglycerides. Urine volume and urinary glucose, protein, osmolarity, electrolytes (Na, K, Cl), BUN and creatinine are measured.

The SGLT inhibitors and other antidiabetic agents, such as RXR agonists, have distinct mechanisms of action. Improved glycemic control, measured as a decrease in plasma glucose, HbA1c, plasma insulin, or plasma triglycerides, or a combination thereof, can be observed at lower concentrations of RXR agonists when given in combination with an SGLT inhibitor. Therefore, a leftward shift in the dose-response curve for effect of RXR agonists on the above parameters can become apparent. In addition, the weight gain observed following treatment with RXR agonists is less pronounced when given with the SGLT inhibitor, since SGLT inhibitors' promotion of the urinary excretion of glucose and loss of calories from the body is demonstrated by reduction in weight or weight gain. Also, since SGLT inhibitors promote a mild diuresis, the edema (and the edematous weight gain) commonly observed after treatment with RXR agonists can be less pronounced or absent. This can be demonstrated by a reduction in the RXR agonist-induced increase in heart weight. A reduction in the amount of RXR agonists necessary to achieve efficacy in turn improves the side-effect profile. The decreased side effects can include such conditions as fatty liver, increased liver weight, body weight gain, heart weight gain, edema, cardiac hypertrophy, hepatohypertrophy, hypoglycemia, and hepatotoxicity, or any combination thereof.

The above examples can also show that the oral administration of an SGLT inhibitor in combination with an antidiabetic agent, such as an RXR modulator, may improve the status of other markers of diabetes mellitus including glycosylated hemoglobin (Hgb A1C) levels. Particularly, the oral administration of an SGLT inhibitor in combination with one or more antidiabetic agents can reduce body weight or body weight gain as well as liver weight or liver weight gain, compared to administration of one or antidiabetic agents alone.

Thus, for treating diabetes, particularly Type II diabetes mellitus, or Syndrome X, a compound of Formula (II) in combination with one or more antidiabetic agents, such as RXR agonists or antagonists that increase insulin sensitivity, may be employed comprising administering repeated oral doses of the compound of formula I in the range of about 25 to 1000 mg once or twice daily and repeated doses of the anti-diabetic agent or agents at jointly effective dosages. The jointly effective dosage for antidiabetic agents disclosed herein may be readily determined by those skilled in the art based on standard dosage guidelines. In particular, such combined administration can be effective to accomplish reduction of body weight, body weight gain, liver weight, or liver weight gain in the subject.

Additionally, a method comprising (a) administering to a subject a jointly effective amount of a glucose reabsorption inhibitor; and (b) administering to the subject a jointly effective amount of an antidiabetic agent, such as an RXR modulator, can be used to reduce body weight, body weight gain, or liver weight of the subject in need thereof, wherein the combined administration can be in any order and the combined jointly effective amounts provide the desired therapeutic effect.

Also, a method comprising (a) administering to a subject a jointly effective amount of a glucose reabsorption inhibitor; and (b) administering to the subject a jointly effective amount of an antidiabetic agent, such as an RXR modulator, can be used to control body weight, body weight gain, liver weight, or liver weight gain of the subject having diabetes, Syndrome X, or associated symptoms or complications, wherein the combined administration can be in any order and the combined jointly effective amounts providing the desired therapeutic effect.

Optimal dosages to be administered may be readily determined by those skilled in the art, and will vary with the particular compound used, the mode of administration, the strength of the preparation and the advancement of the disease condition. In addition, factors associated with the particular patient being treated, including patient's sex, age, weight, diet, time of administration and concomitant diseases, will result in the need to adjust dosages.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

TABLE 3

| Example # | CHOK-SGLT1<br>% Inh (10 uM) | CHOK-SGLT2<br>IC50 (uM) ± SEM |
|---|---|---|
| 1 | 48 | 0.458 ± 0.061 |
| 19 | inactive | 0.532 ± 0.047 |
| 13 | 52 | 0.491 ± 0.056 |
| 15 | 47 | 0.754 ± 0.069 |
| 18 | 43 | 1.2 ± 0.071 |
| 21 | inactive | 0.959 ± 0.118 |
| 6 | 7 | 1* |
| 3 | inactive | 1.59 ± 0.025 |
| 10 | 5 | 2.0 ± 0.071 |
| 14 | 42 | 1.5 ± 0.071 |
| 5 | inactive | 3.25 ± 0.461 |
| 4 | 18 | 1.95 ± 0.816 |
| 9 | 11 | 3.05 ± 0.319 |
| 8 | inactive | 67% Inh. @ 10 μM |
| 2 | 14 | 69% Inh. @ 10 μM |
| 11 | 12 | 66% Inh. @ 10 μM |
| 20 | 38 | 64% Inh. @ 10 μM |
| 17 | inactive | 67% Inh. @ 10 μM |
| 7 | inactive | 43% Inh. @ 10 μM |
| 22 | inactive | 40% Inh. @ 10 μM |
| 12 | inactive | 36% Inh. @ 10 μM |
| 16 | inactive | 42% Inh. @ 10 μM |

*tested once only.

What is claimed is:

1. A method for treating diabetes or Syndrome X, or associated symptoms or complications thereof in a subject, comprising
(a) administering to said subject a jointly effective amount of a compound of formula (II)

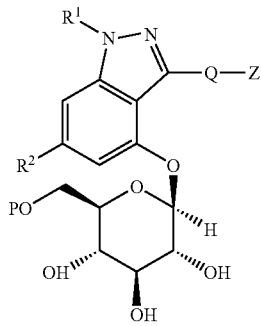

wherein
$R^1$ is H or $C_{1-4}$ alkyl;
$R^2$ is H, F, Cl, methoxy, or $C_{1-3}$ alkyl;
Q is —$(CH_2)_n$— where n=0, 1, or 2; or, where $R^2$ is H, F, Cl, or methoxy, then Q can also be selected from —$CH_2$—S—;
Z is substituted or unsubstituted, and is selected from $C_{3-7}$ cycloalkyl, phenyl, benzhydryl, 5- or 6-membered heteroaryl having 1 or 2 heteroatoms independently selected from N, O, and S, a biaryl, and a 9- or 10-membered fused bicyclyl or fused heterobicyclyl, wherein each fused heterobicyclyl has between 1 and 4 heteroatoms independently selected from N, O, and S;
P=H or acetyl;
or a pharmaceutically acceptable salt thereof,
(b) administering to said subject a jointly effective amount of a second antidiabetic agent, and
(c) administering to said subject a jointly effective amount of a third antidiabetic agent.

2. The method of claim 1, wherein the third antidiabetic agent is selected from
(aa) insulins,
(bb) insulin analogues;
(cc) insulin secretion modulators, and
(dd) insulin secretagogues.

3. The method of claim 1, wherein the second antidiabetic agent is an RXR agonist.

4. The method of claim 1, wherein the diabetes or Syndrome X, or associated symptoms or complications thereof is selected from IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

5. The method of claim 1, wherein the diabetes or Syndrome X, or associated symptoms or complication thereof is IDDM.

6. The method of claim 1, wherein the diabetes or Syndrome X, or associated symptoms or complications thereof is NIDDM.

7. The method of claim 1, wherein the diabetes or Syndrome X, or associated symptoms or complications thereof is IGT or IFG.

8. The method of claim 1, wherein $R^1$ is H.

9. The method of claim 1, wherein $R^2$ is H, methyl, or ethyl.

10. The method of claim 1, wherein Q is —$(CH_2)_n$— and n is 1 or 2.

11. The method of claim 1, wherein Z is independently substituted with between 1 and 3 substituents independently selected from $C_{1-4}$ alkoxy, $C_{1-4}$ alkyl, $C_{3-6}$ cycloalkyl, halo, hydroxy, cyano, amino, $C_{1-4}$ alkylthio, $C_{1-4}$ aminoalkyl, mono- and di($C_{1-4}$ alkyl)amino, phenyl, 5-6 membered heterocyclyl containing between 1 and 3 heteroatoms independently selected from N, S, and O; and wherein the substituent(s) on Z can be further independently substituted with between 1 and 3 substituents independently selected from $C_{1-4}$ alkoxy, $C_{1-4}$ alkyl, halo, hydroxy, cyano, amino, $C_{1-4}$ alkylthio, phenoxy, —$CONR^aR^b$, —$NHSO_2R^a$, and —$SO_2NR^aR^b$ where each of $R^a$ and $R^b$ is independently selected from H and $C_{1-4}$ alkyl.

12. The method of claim 1, wherein Z is phenyl, cyclopentyl, cyclohexyl, 4-substituted cyclohexyl, 2- or 3-substituted cyclopentyl, 4-substituted phenyl, 3,4-disubstituted phenyl, substituted thiophenyl, thiophenyl, biaryl, benzofuranyl, dihydrobenzofuranyl, 4-substituted pyridyl, benzo[b]thienyl, benzothiophenyl, indanyl, naphthyl, 5,6,7,8-tetrahydronapthyl, 1,2,3,4-tetrahydronaphthyl, or benzo[1,4]dioxan.

13. The method of claim 1, wherein Z is unsubstituted or substituted with between 1 and 2 substituents independently selected from methoxy, ethoxy, fluoro, chloro, methyl, ethyl, propyl, isopropyl, cyclopropyl, and phenyl.

14. The method of claim 1, wherein Z is biphenyl, 4-ethylphenyl, (4-propyl)phenyl, 4-methoxyphenyl, 4-ethoxyphenyl, 4-methylthiophenyl, benzofuran-5-yl, dihydrobenzofuran-5-yl, naphthyl, or dihydrobenzofuran-6-yl, or (5-ethylthio)phenyl.

* * * * *